United States Patent
Bejar et al.

(10) Patent No.: US 11,015,223 B2
(45) Date of Patent: May 25, 2021

(54) METHODS FOR DETERMINING RESPONSE TO A HYPOMETHYLATING AGENT

(71) Applicants: THE REGENTS OF THE UNIVERSITY OF CALIFORNIA, Oakland, CA (US); DANA-FARBER CANCER INSTITUTE, INC., Boston, MA (US); THE BRIGHAM AND WOMEN'S HOSPITAL, INC., Boston, MA (US)

(72) Inventors: Rafael Bejar, La Jolla, CA (US); Benjamin Ebert, Brookline, MA (US); Donna Neuberg, Brookline, MA (US); Kristen Stevenson, Waltham, MA (US)

(73) Assignees: THE REGENTS OF THE UNIVERSITY OF CALIFORNIA, Oakland, CA (US); DANA-FARBER CANCER INSTITUTE, INC., Boston, MA (US); THE BRIGHAM AND WOMEN'S HOSPITAT . INC, Boston, MA (US)

( * ) Notice: Subject to any disclaimer, the term of this patent is extended or adjusted under 35 U.S.C. 154(b) by 150 days.

(21) Appl. No.: 14/888,389

(22) PCT Filed: May 12, 2014

(86) PCT No.: PCT/US2014/037717
§ 371 (c)(1),
(2) Date: Oct. 30, 2015

(87) PCT Pub. No.: WO2014/183122
PCT Pub. Date: Nov. 13, 2014

(65) Prior Publication Data
US 2016/0083802 A1    Mar. 24, 2016

Related U.S. Application Data

(60) Provisional application No. 61/822,159, filed on May 10, 2013.

(51) Int. Cl.
C12Q 1/68 (2018.01)
C12Q 1/6886 (2018.01)
C12Q 1/6883 (2018.01)

(52) U.S. Cl.
CPC ......... *C12Q 1/6886* (2013.01); *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2011/0263523 A1    10/2011    Viguie et al.

FOREIGN PATENT DOCUMENTS

WO    2012174419 A2    12/2012

OTHER PUBLICATIONS

Bejar et al, New England Journal of Medicine, 2011, vol. 364, pp. 2496-2506, including supplementary appendix.*
Müller and Florek; Small Molecules in Oncology, 2010, Chapter 11,, pp. 159-170, Springer.*
International Search Report and Written Opinion for PCT/US2014/037717, dated Oct. 10, 2014, 10 pages.
Bejar, et al., "Next-Generation Sequencing of 213 MDS Patient Samples Identifies Mutation Profiles Associated with Response to Hypomethylating Agents and Overall Survival", The MDS Beacon, MDS Symposium 2013, Abstract O-024, May 11, 2013, 2 pages.
Itzykson, et al., "Prognostic Score Including Gene Mutations in Chronic Myelomonocytic Leukemia, vol. 31, No. 19", Jul. 1, 2013, pp. 2428-2436.
Shih, et al., "Molecular Biology of Myelodysplastic Syndromes", Seminars in Oncology, vol. 38, No. 5, Oct. 2011, pp. 613-620.
Traina, et al., "Impact of Molecular Mutations on Treatment Response to Hypomethylating Agents in MDS", Blood. vol. 18, No. 21, Abstract 461, Nov. 18, 2011, 1 page.
Voso, et al., "Why Methylation is Not a Marker Predictive of Response to Hypomethylating Agents", Haematologica vol. 99, No. 4, Apr. 1, 20104, pp. 613-619.
International Preliminary Report on Patentability dated Nov. 19, 2015 for PCT/US2014/037717, Nov. 19, 2015, 8 pages.
Carter, et al., "Absolute quantification of somatic DNA alterations in human cancer", Nature Biotechnology, vol. 30, No. 5, 2012, 413-421.
Cibulskis, et al., "Sensitive Detection of Somatic Point Mutations in Impure and Heterogeneous Cancer Samples", Nature Biotechnology, vol. 31, No. 3, Mar. 2013, 213-219.

* cited by examiner

*Primary Examiner* — Jehanne S Sitton
(74) *Attorney, Agent, or Firm* — Johnson, Marcou, Isaacs & Nix, LLC; F. Brent Nix, Esq.; Michael B. Scher, Esq.

(57) ABSTRACT

Disclosed are methods for predicting a response of a subject with myelodysplastic syndrome to treatment with a hypomethylating agent, for example using a sample obtained from the subject. The methods can be used to select a subject for treatment with a hypomethylating agent, and/or measure a subject's response to therapy and/or disease progression/regression. The methods include detecting, in a nucleic acid sample obtained from a subject, one or more mutations of any one or more genes selected from Table 3a.

7 Claims, 7 Drawing Sheets

- *TET2* mutation

- *ASXL1* mutation

- *TET2* & *ASXL1* mutation

- Others

Response rate unchanged
*TET2* mutation ratio falls

Response rate higher

Response rate higher
*ASXL1* mutation ratio rises

Response rate unchanged to lower

US 11,015,223 B2

METHODS FOR DETERMINING RESPONSE TO A HYPOMETHYLATING AGENT

CROSS-REFERENCE TO RELATED APPLICATION

This application claims the priority benefit of the earlier filing date of U.S. Provisional Application No. 61/822,159, filed May 10, 2013, which is hereby incorporated herein by reference in its entirety.

STATEMENT OF GOVERNMENT SUPPORT

This application is the U.S. National Stage of International Application No. PCT/US2014/037717, filed May 12, 2014, published in English under PCT Article 21(2), which claims the priority benefit of the earlier filing date of U.S. Provisional Application No. 61/822,159, filed May 10, 2013, which is hereby incorporated herein by reference in its entirety.

FIELD OF THE DISCLOSURE

This disclosure relates to the field of cancer chemotherapy and in particular, to methods for predicting if a subject would benefit from therapy with a DNA hypomethylating agent.

BACKGROUND

Myelodysplastic syndromes (MDS) are a heterogeneous group of hematologic disorders characterized by ineffective hematopoiesis and dysplasia. It is a hematological disorder in which genomic abnormalities accumulate in a hematopoietic stem cell leading to peripheral cytopenias of varying degrees of severity, as a consequence of multilineage differentiation impairment, and, in the early phases, bone marrow (BM) apoptosis. Morbidity and mortality in the disease results from cytopenias or transformation to acute myeloid leukemia (AML), which may both lead to serious infectious diseases, anemia or hemorrhage caused by dysfunction and reduction of blood cells. There are associated cytogenetic abnormalities, including deletions of chromosomes 5, 7, amongst others.

Patients with MDS often develop severe anemia and require frequent blood transfusions. In most cases, the disease worsens and the patient develops cytopenias (low blood counts) caused by progressive bone marrow failure. The myelodysplastic syndromes are all disorders of the stem cell in the bone marrow. In MDS, hematopoiesis (blood production) is disorderly and ineffective. The number and quality of blood-forming cells decline irreversibly, further impairing blood production.

The initial hematopoietic stem cell injury can be from causes such as, but not limited to, cytotoxic chemotherapy, radiation, virus, chemical exposure, and genetic predisposition. A clonal mutation predominates over bone marrow, suppressing healthy stem cells. In the early stages of MDS, the main cause of cytopenias is increased programmed cell death (apoptosis). As the disease progresses and converts into leukemia, gene mutation rarely occurs and a proliferation of leukemic cells overwhelms the healthy marrow. The disease course differs, with some cases behaving as an indolent disease and others behaving aggressively with a very short clinical course that converts into an acute form of leukemia.

SUMMARY OF THE DISCLOSURE

Disclosed are methods for predicting a response of a subject with myelodysplastic syndrome to treatment with a hypomethylating agent, for example using a sample obtained from the subject. The methods can be used to select a subject for treatment with a hypomethylating agent, and/or measure a subject's response to therapy and/or disease progression/regression. The methods include detecting, in a nucleic acid sample obtained from a subject, one or more mutations of any one or more genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1. Detecting a mutation in anyone of TET2, RUNX1, TP53, SRSF2, NOTCH2, NRAS, BCOR, MAML1, TLR1, PHF6, ZRSR2, NPM1, WT1, GATA2, and MYBL2 indicates that the subject will respond to treatment with a hypomethylating agent as compared to a subject without the mutation and detecting a mutation in anyone of ASXL1, DNMT3A, SF3B1, U2AF1, NF1, EZH2, NOTCH1, IDH2, SCAF11, KDM6B, CBL, ATRX, KDM3A, PRPF8, PTPN11, IDH1, JAK2, KRAS, TLR6, U2AF2, TLR2, TLR4, SF3B3, SUZ12, indicates that the subject will not respond to treatment with a hypomethylating agent as compared to a subject without the mutation. In some examples, the methods include, detecting mutations in any two or more genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1. In specific examples, the presence of a mutation in TET2 and the absence of a mutation is ASXL1 indicates that the subject will respond to a hypomethylating agent. In other specific examples, the presence of a mutation in the CBL gene indicates that the subject will not respond to treatment with a hypomethylating agent. In still other specific examples, the presence of a mutation in the NRAS gene indicates that the subject will respond to treatment with a hypomethylating agent.

In some embodiments, the allelic frequency of the mutations is determined. An increased allelic frequency of mutations in any one of TET2, RUNX1, TP53, SRSF2, NOTCH2, NRAS, BCOR, MAML1, TLR1, PHF6, ZRSR2, NPM1, WT1, GATA2, and MYBL2 indicates that the subject will respond to treatment with a hypomethylating agent as compared to a subject with lower allelic frequency of the mutation and an increased allelic frequency of mutations in any one of ASXL1, DNMT3A, SF3B1, U2AF1, NF1, EZH2, NOTCH1, IDH2, SCAF11, KDM6B, CBL, ATRX, KDM3A, PRPF8, PTPN11, IDH1, JAK2, KRAS, TLR6, U2AF2, TLR2, TLR4, SF3B3, SUZ12, indicates that the subject will not respond to treatment with a hypomethylating agent as compared to a subject with lower allelic frequency of the mutation.

Also disclosed are kits for detecting mutations and/or the allelic frequency of such mutations in genes selected from ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1. A myelodysplastic syndrome (MDS) expression profile, comprising a pattern of mutations of one or more genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1 and machine readable media containing one or more of such MDS expression profiles.

BRIEF DESCRIPTION OF THE FIGURES

FIG. 2A, Quantitative measure of variant containing reads estimates the abundance of these mutations (uncorrected for allele copy number). Mutations of TET2, TP53, and splicing factor genes are often present in the dominant clone while mutations of tyrosine kinase signaling genes are often present in smaller clones. Mutations of ASXL1 are more widely distributed. FIG. 2B, Analysis of samples with both TET2 and ASXL1 mutations indicate that ASXL1 mutations are most often co-dominant with or smaller than TET2 mutant clones.

FIG. 4B, Survival of patients with and without TP53 mutations. FIG. 4C, Survival of patients with and without PTPN11 mutations.

DETAILED DESCRIPTION OF SEVERAL EMBODIMENTS

I. Summary of Terms

Figure 1:
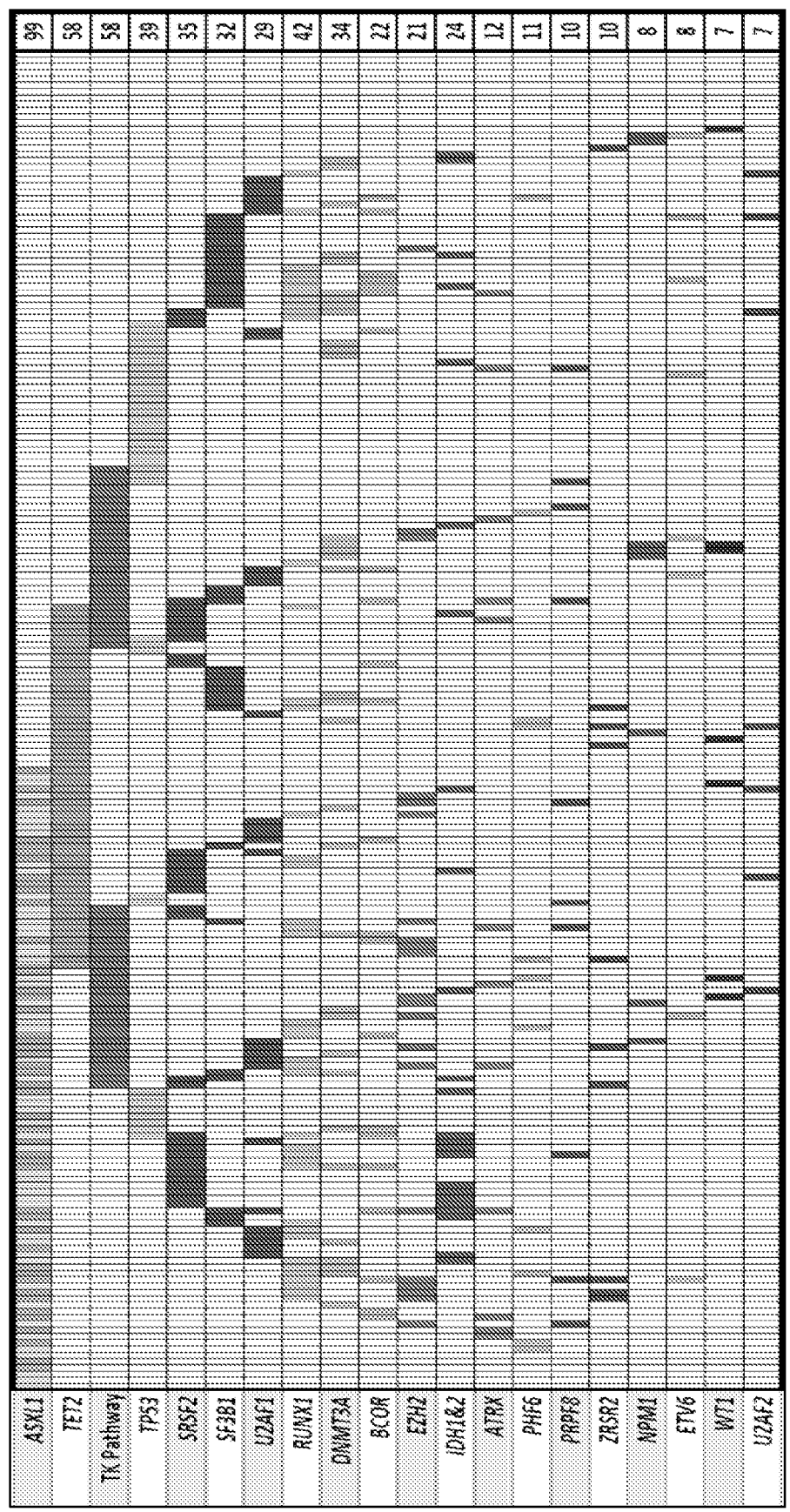
FIG. 1 is a table showing the spectrum of mutations in 213 patients in select MDS associated genes. Each column represents an individual patient sample and each colored cell represents a mutation of the gene or gene group listed to left of that row. The number of mutations for each row is indicated in the column to the right. TK Pathway=NRAS, KRAS, CBL, CBLB, JAK2, PTPN11, BRAF, MPL, KIT.

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

To facilitate review of the various embodiments of this disclosure, the following explanations of specific terms are provided.

Accuracy: Refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

Administration: To provide or give a subject an agent, such as a chemotherapeutic agent, for example a hypomethylating agent, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Amplification: To increase the number of copies of a nucleic acid molecule. The resulting amplification products are called "amplicons." Amplification of a nucleic acid molecule (such as a DNA or RNA molecule encoding targeting probe) refers to use of a technique that increases the number of copies of a nucleic acid molecule (including fragments).

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Binding or stable binding (of an oligonucleotide): An oligonucleotide, such as a nucleic acid probe or primer that specifically binds to a nucleic acid target, such as target mutation, binds or stably binds to a target nucleic acid, if a sufficient amount of the oligonucleotide forms base pairs or is hybridized to its target nucleic acid. Binding can be detected by either physical or functional properties.

Clinical parameters or risk factor: Non-sample or non-analyte biomarkers of subject health status or other characteristics, such as, without limitation, age (Age), ethnicity (RACE), gender (Sex), family history (FamHX), International Prognostic Scoring System (IPSS) score, karyotype, blast proportion or cytopenia.

Contacting: Placement in direct physical association, including both in solid or liquid form, for example contacting a sample with a nucleic acid probe and/or primer.

Control: A reference standard. A control can be a known value or range of values indicative of basal levels or amounts or present in a tissue or a cell or populations thereof. A control can also be a cellular or tissue control, for example a tissue from a non-diseased state. A difference between a test sample and a control can be an increase or conversely a decrease, for example an increase or decrease in the number of mutations. The difference can be a qualitative difference or a quantitative difference, for example a statistically significant difference.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Detect: To determine if an agent (such as a signal or particular nucleic acid mutation or set of mutations) is present or absent. In some examples, this can further include quantification, such as the allelic frequency in a sample, or a fraction of a sample, such as a particular cell or cells within a tissue.

Detectable label: A compound or composition that is conjugated directly or indirectly to another molecule to facilitate detection of that molecule. Specific, non-limiting examples of labels include fluorescent tags, enzymatic linkages, and radioactive isotopes. In some examples, a label is attached to an antibody or nucleic acid to facilitate detection of the molecule the antibody or nucleic acid specifically binds.

DNA sequencing: The process of determining the nucleotide order of a given DNA molecule. Generally, the sequencing can be performed using automated Sanger sequencing (AB13730xl genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®).

In some embodiments, DNA sequencing is performed using a chain termination method developed by Frederick Sanger, and thus termed "Sanger based sequencing" or "SBS." This technique uses sequence-specific termination of a DNA synthesis reaction using modified nucleotide substrates. Extension is initiated at a specific site on the template DNA by using a short oligonucleotide primer complementary to the template at that region. The oligonucleotide primer is extended using DNA polymerase in the presence of the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is present. The fragments are then size-separated by electrophoresis a polyacrylamide gel, or in a narrow glass tube (capillary) filled with a viscous polymer. An alternative to using a labeled primer is to use labeled terminators instead; this method is commonly called "dye terminator sequencing."

"Pyrosequencing" is an array based method, which has been commercialized by 454 Life Sciences. In some embodiments of the array-based methods, single-stranded DNA is annealed to beads and amplified via EmPCR®. These DNA-bound beads are then placed into wells on a fiber-optic chip along with enzymes that produce light in the presence of ATP. When free nucleotides are washed over this chip, light is produced as the PCR amplification occurs and ATP is generated when nucleotides join with their complementary base pairs. Addition of one (or more) nucleotide(s) results in a reaction that generates a light signal that is recorded, such as by the charge coupled device (CCD) camera, within the instrument. The signal strength is proportional to the number of nucleotides, for example, homopolymer stretches, incorporated in a single nucleotide flow.

Formula, algorithm or model: Any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use is linear and non-linear equations and statistical classification analyses to determine the relationship between mutations of signature gene nucleic acids detected in a subject sample and the subject's response to the a hypomethylating agent. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful either combined with a selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art.

High throughput technique: Through a combination of robotics, data processing and control software, liquid handling devices, and detectors, high throughput techniques allows the rapid identification of mutations present in samples, such as samples from a subject with MDS.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or it's analog) and the DNA, or RNA. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Hypomethylating agent: A compound that inhibits DNA methylation, for example when administered to a subject, such as a subject with MDS. Examples of hypomethylating agents for use in treating MDS include decitabine (5-aza-2'-deoxycytidine) and azacytidine (5-azacytidine). While not being bound by theory, hypomethylating agents are believed to inhibit the activity of methyltransferase at low doses, causing hypomethylation of DNA which prevents normal DNA synthesis and results in subsequent cytotoxicity.

Inhibiting or treating a disease: Inhibiting the full development of a disease or condition, for example, in a subject who is at risk for a disease such cancer, or MDS. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components in the cell of the organism in which the component naturally occurs, for example, extra-chromatin DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Mutated gene or mutation: An allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant. The term "mutation" means any base pair change in the nucleic acid sequence whether it changes the protein's structure or function or has no effect compared to wild type sequence. The term "germline mutation", as used herein, indicates a deleterious alteration in one gene allele which is present in every nucleus containing cell of the body. The term "somatic mutation" refers to an alteration in at least one gene allele that is not found in every cell of the body, but is found only in isolated cells. A characteristic of the somatic mutations as used herein is, that they are restricted to particular tissues or even parts of tissues or cells within a tissue and are not present in the whole organism harboring the tissues or cells. Examples of somatic mutations include mutations produced by mismatch incorporations of nucleotides during replication of the genomic DNA in the course of the cell division cycle of proliferating cells.

Nucleic acid (molecule or sequence): A deoxyribonucleotide or ribonucleotide polymer including without limitation, cDNA, mRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties, and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Probes and primers: A probe comprises an isolated nucleic acid capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 20-70 nucleotides, 20-60 nucleotides, 20-50 nucleotides, 20-40 nucleotides, or 20-30 nucleotides.

Primers are short nucleic acid molecules, for instance DNA oligonucleotides are 10 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein. It is also appropriate to generate probes and primers based on fragments or portions of these disclosed nucleic acid molecules, for instance regions that encompass the identified polymorphisms of interest. PCR primer pairs can be derived from a known sequence by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Sample: A sample, such as a biological sample, that includes biological materials (such as nucleic acids) obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as MDS). For example, a biological sample can be bone marrow, tissue biopsies, whole blood, serum, plasma, blood cells, endothelial cells, circulating tumor cells, lymphatic fluid, ascites fluid, interstitial fluid (also known as "extracellular fluid" and encompasses the fluid found in spaces between cells, including, inter alia, gingival crevicular fluid), cerebrospinal fluid (CSF), saliva, mucous, sputum, sweat, urine, Statistically significant: An alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

Subject: A mammal. The mammal can be a human, non-human primate, mouse, rat, dog, cat, horse, or cow, but are not limited to these examples. Mammals other than humans can be advantageously used as subjects that represent animal models of tumor metastasis. A subject can be male or female. A subject can be one who has been previously diagnosed or identified as having hematological disorders, such as MDS, and optionally has already undergone, or is undergoing, a therapeutic intervention for the disease. Alternatively, a subject can also be one who has not been previously diagnosed as having hematological disorders, such as MDS. For example, a subject can be one who exhibits one or more risk factors for hematological disorders, such as MDS.

Therapeutically effective amount: The quantity of a composition, such as a hypomethylating agent, sufficient to achieve a desired effect in a subject being treated. For instance, this can be the amount necessary to inhibit the progression of MDS or to measurably alter outward symptoms of MDS. When administered to a subject, a dosage will generally be used that will achieve target tissue concentrations that has been shown to achieve in vitro inhibition of or to measurably alter outward symptoms of MDS.

Wild-type: A gene or a gene product that has the characteristics of that gene or gene product when isolated from a naturally occurring source. A wild-type gene is that which is most frequently observed in a population and is thus arbitrarily designated the "normal" or "wild-type" form of the gene. "Wild-type" can also refer to the sequence at a specific nucleotide position or positions, or the sequence at a particular codon position or positions, or the sequence at a particular amino acid position or positions. As used herein, "mutant," "modified" or "polymorphic" refers to a gene or gene product which displays modifications in sequence and/or functional properties when compared to the wild-type gene or gene product. "Mutant," "modified" or "polymorphic" also refers to the sequence at a specific nucleotide position or positions, or the sequence at a particular codon position or positions, or the sequence at a particular amino acid position or positions.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting II. Description of Several Embodiments A. Introduction Hypomethylating agents, such as 5-azacytidine or decitabine, have been a major breakthrough in the treatment of patients with myelodysplastic syndromes (MDS). They have been shown to improve transfusion requirements and to change the natural history of the disease. However, with increasing cumulative clinical experience, it has become apparent that there is a subgroup of patients who do not respond to hypomethylating agents.

Fewer than half of myelodysplastic syndromes (MDS) patients respond to treatment with hypomethylating agents, but highly predictive biomarkers of response have not been identified. Prior to this disclosure, election of therapy was largely empiric but must take into account the age, comorbidities, and performance status of the patient, as well as the characteristics of the disease at the time of treatment. Thus there is a need for diagnostic approaches to determine which cohort of patients would benefit from hypomethylating therapy and conversely which would not. For example, those predicted to respond can be placed on hypomethylating therapies while those predicted non-responders would be placed on alternate therapeutic regimes. This is especially true given the side effects of such hypomethylating agents. This disclosure meets those needs.

The inventors have identified a set of signature genes that when somatically mutated can be associated with a subject's response to hypomethylating agents, such as decitabine and azacitidine. In some examples, the presence of mutations in certain genes is indicative of a positive response to hypomethylating agents, for example a positive response of a subject with a hematological disorder, such as myelodysplastic syndromes (MDS), acute myelogenous leukemia (AML), Acute lymphoblastic leukemia (ALL), Chronic lymphocytic leukemia (CLL), Chronic myelogenous leukemia (CML). In some examples, the presence of mutations in certain genes is indicative of a negative response to hypomethylating agents, for example a positive response of a subject with a hematological disorder, such as myelodysplastic syndromes (MDS), acute myelogenous leukemia (AML), Acute lymphoblastic leukemia (ALL), Chronic lymphocytic leukemia (CLL), Chronic myelogenous leukemia (CML).

The inventors were able to use next generation sequencing and computational analysis to detect somatic mutations and determine the relevance of these mutations to a subject's sensitivity to hypomethylating agents. While a few of the genes discovered by the inventors to be associated with response to hypomethylating have previously been found in subjects with MDS, prior to this disclosure, the significance of the mutations in this set of genes with regards to response to hypomethylating agents was unknown.

Disclosed herein are methods for predicting the response of a subject with a hematological disorder, such as myelodysplastic syndromes (MDS), to treatment with a hypomethylating agent. The methods disclosed herein can be used to identify a subject that would benefit from therapy with a hypomethylating agent, such as subject diagnosed with MDS. The methods can further be used to select a subject for treatment with a hypomethylating agent. In some examples, the methods can be used to monitor response to a therapy with a hypomethylating agent, for example to determine if a subject would benefit from continued treatment with a hypomethylating agent or should discontinue treatment in favor of an alternate treatment.

B. Methods

Disclosed herein is a method for predicting a response of a subject with a hematological disorder, such as myelodysplastic syndrome (MDS), acute myelogenous leukemia (AML), Acute lymphoblastic leukemia (ALL), Chronic lymphocytic leukemia (CLL), Chronic myelogenous leukemia (CML) to treatment with a hypomethylating agent. The methods include detecting in a nucleic acid sample obtained from a subject, one or more mutations of any one or more genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1, wherein detecting a mutation in anyone of TET2, RUNX1, TP53, SRSF2, NOTCH2, NRAS, BCOR, MAML1, TLR1, PHF6, ZRSR2, NPM1, WT1, GATA2, and MYBL2 indicates that the subject will respond to treatment with a hypomethylating agent as compared to a subject without the mutation and wherein the presence of ASXL1, DNMT3A, SF3B1, U2AF1, NF1, EZH2, NOTCH1, IDH2, SCAF11, KDM6B, CBL, ATRX, KDM3A, PRPF8, PTPN11, IDH1, JAK2, KRAS, TLR6, U2AF2, TLR2, TLR4, SF3B3, SUZ12, indicates that the subject will not respond to treatment with a hypomethylating agent as compared to a subject without the mutation.

All or a portion of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1 may be used to predict response to a hypomethylating agent. In some examples of the method, mutations are detected in two or more genes, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, or all 68 of the genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1. In specific examples, the presence of a mutation in TET2 and the absence of a mutation in ASXL1 indicates that the subject will respond to a hypomethylating agent. In other examples, the presence of a mutation in the CBL gene indicates that the subject will not respond to treatment with a hypomethylating agent. In still other examples, the presence of a mutation in the NRAS gene indicates that the subject will respond to treatment with a hypomethylating agent.

The mutational status of the genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1 may be defined in combination with corresponding scalar weights on the real scale with varying magnitude, which are further combined through linear or non-linear, algebraic, trigonometric or correlative means into a single scalar value via an algebraic, statistical learning, Bayesian, regression, or similar algorithms which together with a mathematically derived decision function on the scalar value provide a predictive model by which mutational status profiles from samples may be resolved into discrete classes of responder or non-responder, resistant or non-resistant, to a hypomethylating agent. Such predictive models, are developed by learning weights and the decision threshold, optimized for sensitivity, specificity, negative and positive predictive values, hazard ratio or any combination thereof, under cross-validation, bootstrapping or similar sampling techniques, from a set of representative expression profiles from historical patient samples with known drug response and/or resistance. In one embodiment, the mutational status of genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1 are used to form a weighted sum of their signals, where individual weights can be positive or negative. The resulting sum ("decisive function") is compared with a pre-determined reference point or value. The comparison with the reference point or value may be used to diagnose, or predict a clinical condition or outcome.

In some embodiments, the nucleic acid sample is isolated from blood, bone marrow or a blood fraction obtained from the subject. In some embodiments, detecting mutations is performed by Next-Generation genomic sequencing and/or Mass spectrometry genotyping. In specific examples, the mutations are identified using next generation sequencing of samples and computational analysis of the sequence reads using methods described in Cibulskis et al., *Nature Biotechnology* 31, 213-219 (2013) and Carter et al., *Nat Biotechnol.* 30(5):413-21 (2012), which are both specifically incorporated herein by reference in their entirety. In some embodiments, a hypomethylating agent is administered to the subject. In some embodiments, a mutation is not a silent mutation. In some embodiments a mutation is not a germline mutation. In some embodiments, the mutations identified are somatic mutations. In some embodiments a nucleic acid sample is obtained from the subject.

As disclosed herein the allelic frequency the mutations in one or more of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1 genes is correlated to response to a hypomethylating agent. By way of example and shown in the Examples below, in the case of TET2 mutations, an increase in the allelic frequency of TET2 mutations in subject indicates that the subject will be more responsive to a hypomethylating agent than a subject with low allelic frequency of TET2 mutations. Thus, in some examples the disclosed methods further include determining the allelic frequency of the mutations in one or more genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1. In some examples, an increased allelic frequency of mutations in any one of TET2, RUNX1, TP53, SRSF2, NOTCH2, NRAS, BCOR, MAML1, TLR1, PHF6, ZRSR2, NPM1, WT1, GATA2, and MYBL2 indicates that the subject will respond to treatment with a hypomethylating agent as compared to a subject with lower allelic frequency of the mutation. In some examples, the allelic frequency is used as a cut off for selection of a therapy. In some examples, the allelic frequency used as a cut off is about 0.001 or greater, such as greater than about 0.001, 0.01, 0.02, 0.05, 0.1, 0.25, or 0.5. In other words, a subject having an allelic frequency of greater than about 0.001 of a mutation associated with a positive response is selected for treatment with a hypomethylating agent. In some examples, an increased allelic frequency of mutations in any one of ASXL1, DNMT3A, SF3B1, U2AF1, NF1, EZH2, NOTCH1, IDH2, SCAF11, KDM6B, CBL, ATRX, KDM3A, PRPF8, PTPN11, IDH1, JAK2, KRAS, TLR6, U2AF2, TLR2, TLR4, SF3B3, SUZ12, indicates that the subject will not respond to treatment with a hypomethylating agent as compared to a subject with lower allelic frequency of the mutation. In some examples, the allelic frequency used as a cut off is about 0.001 or greater, such as greater than about 0.001, 0.01, 0.02, 0.05, 0.1, 0.25, or 0.5. In other words, a subject having an allelic frequency of greater than about 0.001 of a mutation associated with a negative response is not selected for treatment with a hypomethylating agent. In specific examples, an increased allelic frequency of mutations in TET2 indicates that the subject will respond to treatment with a hypomethylating agent as compared to a subject with lower allelic frequency of the mutation.

In some embodiments the mutant allele frequency is determined by a method selected from the group consisting of Next-Generation sequencing, Mass spectrometry genotyping, real time polymerase chain reaction, single nucleotide polymorphism (SNP) arrays, and interphase fluorescent in situ hybridization (FISH) analysis. In specific examples, the allelic frequency of mutation in one or more of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1 are identified using next generation sequencing of samples and computational analysis of the sequence reads using methods described in Cibulskis et al., *Nature Biotechnology* 31, 213-219 (2013) and Carter et al., *Nat Biotechnol.* 30(5):413-21 (2012), which are both specifically incorporated herein by reference in their entirety.

In some embodiments, a subject is selected for treatment with a hypomethylating agent based on the presence and/or absence of mutations in one or more of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1.

In some embodiments, the disclosed methods are used to assess disease progression, such as the progression of myelodysplastic syndrome (MDS) in a subject, for example during hypomethylation therapy. The methods include determining in a first nucleic acid sample from the subject a mutant allele frequency of one or more of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1; determining in a second nucleic acid sample from the subject a mutant allele frequency in of one or more of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1 with one or more mutations at a second period of time; and comparing the mutant allele frequency determined in the first sample and the second sample, wherein the progression of MDS in the subject is assessed by a change in the mutant allele frequency in the gene comprising at least one mutation detected from the subject. In some examples, the first nucleic acid sample is obtained before administration of a hypomethylating agent and the second nucleic acid sample is obtained before administration of the hypomethylating agent.

Methods of detecting mutant alleles and/or evaluating the mutant allele frequency in a particular gene or chromosomal region are well known to those of skill in the art and include Hybridization-based Assays and Amplification-based Assays and combinations thereof.

Hybridization-based assays include, but are not limited to, traditional "direct probe" methods such as Southern Blots or In Situ Hybridization (e.g., FISH), and "comparative probe" methods such as Comparative Genomic Hybridization (CGH). The methods can be used in a wide variety of formats including, but not limited to substrate—(e.g. membrane or glass) bound methods or array-based approaches as described below.

Generally, in situ hybridization includes; fixation of tissue or biological structure to be analyzed; prehybridization treatment of the biological structure to increase accessibility of target DNA, and to reduce nonspecific binding; hybridization of the mixture of nucleic acids to the nucleic acid in the biological structure or tissue; post-hybridization washes to remove nucleic acid fragments not bound in the hybridization and detection of the hybridized nucleic acid fragments. The reagent used in each of these steps and the conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. The preferred size range is from about 200 bp to about 1000 bases, more preferably between about 400 to about 800 bp for double stranded, nick translated nucleic acids. In some applications it is necessary to block the hybridization capacity of repetitive sequences. Thus, human genomic DNA or Cot-1 DNA is used to block nonspecific hybridization.

In Comparative Genomic Hybridization methods a first collection of nucleic acids is labeled with a first label (for example from a diseased cell/tissue), while a second collection of nucleic acids (for example from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Other Hybridization protocols suitable for use with the methods of disclosed herein are described, e.g., in Albertson (1984) EMBO J. 3: 1227-1234; Pinkel (1988) Proc. Natl. Acad. Sci. USA 85: 9138-9142; EPO Pub. No. 430,402; Methods in Molecular Biology, Vol. 33: In Situ Hybridization Protocols, Choo, ed., Humana Press, Totowa, N.J. (1994) and the like.

The methods of this disclosure are particularly well suited to array-based hybridization formats. Arrays are a multiplicity of different "probe" or "target" nucleic acids (or other compounds) attached to one or more surfaces (e.g., solid, membrane, or gel). The multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) Genome Res. 7: 606-614; Jackson (1996) Nature Biotechnology 14: 1685; Chee (1995) Science 274: 610; WO 96/17958.

Arrays, particularly nucleic acid arrays, can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high density arrays. Arrays can also be produced using oligonucleotide synthesis technology. Thus, for example, U.S. Pat. No. 5,143,854 and PCT patent publication Nos. WO 90/15070 and 92/10092 teach the use of light-directed combinatorial synthesis of high density oligonucleotide arrays. A spotted array can include genomic DNA, e.g. overlapping clones that provide a high resolution scan of the amplicon corresponding to the region of interest. Amplicon nucleic acid can be obtained from, e.g., MACs, YACs, BACs, PACs, Pis, cosmids, plasmids, inter-Alu PCR products of genomic clones, restriction digests of genomic clone, cDNA clones, amplification (e.g., PCR) products, and the like.

The array nucleic acids are derived from previously mapped libraries of clones spanning or including the target sequences of the invention, as well as clones from other areas of the genome, as described below. The arrays can be hybridized with a single population of sample nucleic acid or can be used with two differentially labeled collections (as with an test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

Detection of a hybridization complex may require the binding of a signal generating complex to a duplex of target and probe polynucleotides or nucleic acids. Typically, such binding occurs through ligand and anti-ligand interactions, such as between a ligand-conjugated probe and an anti-ligand conjugated with a signal. The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Amplification-based assays can be used to detect mutant alleles and/or measure mutant allele frequency. In such amplification-based assays, the nucleic acid sequences act as a template in an amplification reaction (e.g. Polymerase Chain Reaction (PCR). In a quantitative amplification, the amount of amplification product will be proportional to the amount of template in the original sample. Comparison to appropriate controls, such as healthy tissue or samples provides a measure of the mutant allele frequency of the desired target nucleic acid sequence. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) PCR Protocols, A Guide to Methods and Applications, Academic Press, Inc. N.Y.).

Other suitable amplification methods include, but are not limited to ligase chain reaction (LCR) (see Wu and Wallace (1989) Genomics 4: 560, Landegren et al. (1988) Science 241: 1077, and Barringer et al. (1990) Gene 89: 117); transcription amplification (Kwoh et al. (1989) Proc. Natl. Acad. Sci. USA 86: 1173); and self-sustained sequence replication (Guatelli et al. (1990) Proc. Nat. Acad. Sci. USA 87: 1874).

Methods of detecting somatic mutations of a particular gene or chromosomal region are well known to those of skill in the art and include Mass spectrometry genotyping and Next-generation sequencing, such as but not limited to pyrosequencing. A variety of methods are available for detecting the presence of mutations in an individual gene or chromosome. Advancements in this field have provided accurate, easy, and inexpensive large-scale genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR.

In one example, the methods further include administering a hypomethylation agent based on the mutational status of one or more mutations of any one or more genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1, wherein detecting a mutation in anyone of TET2, RUNX1, TP53, SRSF2, NOTCH2, NRAS, BCOR, MAML1, TLR1, PHF6, ZRSR2, NPM1, WT1, GATA2, and MYBL2 indicates that the subject will respond to treatment with a hypomethylating agent as compared to a subject without the mutation and wherein the presence of ASXL1, DNMT3A, SF3B1, U2AF1, NF1, EZH2, NOTCH1, IDH2, SCAF11, KDM6B, CBL, ATRX, KDM3A, PRPF8, PTPN11, IDH1, JAK2, KRAS, TLR6, U2AF2, TLR2, TLR4, SF3B3, SUZ12, indicates that the subject will not respond to treatment with a hypomethylating agent as compared to a subject without the mutation.

In some embodiments, once a patient's diagnosis, for example as likely to respond to treatment with a hypomethylating agent is determined, an indication of that diagnosis can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, voltammetric trace, or other diagram), or an audible output.

In other examples, the output is a numerical value. In additional examples, the output is a graphical representation, for example, a graph that indicates the value (such as amount or relative amount) of the mutational status, for example allelic frequency, in the sample from the subject on a standard curve. In a particular example, the output (such as a graphical output) shows or provides a cut-off value or level that indicates whether a particular subject will respond to treatment with a hypomethylating agent. In some examples, the output is communicated to the user, for example by providing an output via physical, audible, or electronic means (for example by mail, telephone, facsimile transmission, email, or communication to an electronic medical record).

The output can provide quantitative information (for example, the allelic frequency) or can provide qualitative information (for example, a diagnosis of response or non-response to a hypomethylating agent). In additional examples, the output can provide qualitative information regarding the allelic frequency in the sample.

In some examples, the output is accompanied by guidelines for interpreting the data, for example, numerical or other limits that response to a hypomethylating agent. The indicia in the output can, for example, include normal or abnormal ranges or a cutoff, which the recipient of the output may then use to interpret the results, for example, to arrive at a diagnosis, prognosis, or treatment plan. In other examples, the output can provide a recommended therapeutic regimen. In some examples, the test may include determination of other clinical information.

In some embodiments, the disclosed methods of diagnosis include one or more of the following depending on the patient's diagnosis: a) prescribing a treatment regimen for the patient; b) not prescribing a treatment regimen for the patient; c) administering a treatment to the patient if the patient's determined diagnosis is considered to be positive for treatment with a hypomethylating agent; and d) not administering a treatment regimen to the patient if the patient's determined diagnosis is considered to be negative for treatment with a hypomethylating agent. In an alternative embodiment, the method can include recommending one or more of a)-d).

Also disclosed is a myelodysplastic syndrome (MDS) mutational status profile, comprising a pattern of mutations of one or more genes selected from the group consisting of ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1. In some embodiments, a machine readable media contains one or more MDS expression profiles, and optionally, additional test results and subject information. A machine-readable storage medium can comprise a data storage material encoded with machine readable data or data arrays which, when using a machine programmed with instructions for using said data, is capable of use for a variety of purposes, such as, without limitation, subject information relating to a hematological disorder, such as MDS risk factors over time or in response drug therapies. Mutations of genes and the mutant allele frequency in genes with at least one mutation can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein.

C. Kits

Disclosed are kits that include reagents for detecting mutations in one or more ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1 genes and reagents for determining the mutant allele frequency in these genes, such as, nucleic acids that specifically identify one or more ASXL1, TET2, RUNX1, TP53, SRSF2, DNMT3A, SF3B1, U2AF1, NOTCH2, NRAS, BCOR, NF1, EZH2, MAML1, NOTCH1, IDH2, SCAF11, KDM6B, CBL, TLR1, ATRX, KDM3A, PHF6, PRPF8, PTPN11, ZRSR2, IDH1, JAK2, KRAS, NPM1, ETV6, TLR6, WT1, U2AF2, TLR2, GATA2, TLR4, MYBL2, SF3B3, SUZ12, CDK6, SF3B2, CEBPA, DDX42, TERT, EED, HNRNPA2B1, PRPF40B, LUC7L2, SF3B14, NCSTN, APH1A, SF3A1, SF3B4, SFRS5, MPL, CBLB, SF1, MYD88, RBBP4, SF3A2, TERC, BRAF, SFRS1, GNAS, KIT, SPOP, and DKC1 nucleic acids by having homologous nucleic acid sequences, such as oligonucleotide sequences, complementary to a portion of the nucleic acids packaged together in the form of a kit. The oligonucleotides can be fragments of the genes. For example the oligonucleotides can be 200, 150, 100, 50, 25, 10 or less nucleotides in length. The kit may contain in separate container or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or a sandwich ELISA as known in the art. Alternatively, the kit contains a nucleic acid substrate array comprising one or more nucleic acid sequences.

The following example is provided to illustrate certain particular features and/or embodiments. These examples should not be construed to limit the invention to the particular features or embodiments described.

EXAMPLE

Methods

Patient Samples and Response Assessment:

A total of 213 MDS patients treated azacitidine or decitabine were included in this study. Samples were obtained from patients treated at the Dana-Farber Cancer Institute (n=42), the MD Anderson Cancer Center (n=104), and as part of the DACO-020 (ADOPT) clinical trial of decitabine (n=67). All samples were collected with patient consent under IRB-approved protocols in accordance with the Declaration of Helsinki. There were no significant differences in baseline patient characteristics by treatment site (Table 1).

TABLE 1

Patient Characteristics and Treatments Received

| | N (%) |
|---|---|
| N | 213 |
| Sample Collection Site | |
| DFCI | 42 (20) |
| ADOPT | 67 (31) |
| MD ANDERSON | 104 (49) |
| Treatments Received | |
| Azacitidine Alone | 42 (20) |
| Decitabine Alone | 144 (68) |
| Decitabine + Other | 27 (13) |
| Age, ≥70 yrs. | 103 (48) |
| Sex | |
| Male | 155 (73) |
| Female | 58 (27) |
| FAB | |
| RA | 30 (14) |
| RARS | 24 (11) |
| RAEB | 125 (59) |
| RAEB-t | 6 (3) |
| CMML | 21 (10) |
| Other | 7 (3) |
| IPSS | |
| Low | 11 (5) |
| Int-1 | 86 (40) |
| Int-2 | 76 (36) |
| High | 37 (17) |
| Unknown | 3 (1) |
| Cytogenetics | |
| Normal or −Y | 107 (50) |
| Complex | 51 (24) |
| −7/7q− isolated or | 14 (7) |
| +8 isolated | 11 (5) |
| 20q− isolated | 7 (3) |
| 5q− isolated or +1 | 3 (1) |
| Other | 13 (6) |
| Unknown | 7 (3) |

Response to treatment was assessed using IWG response criteria revised in 2006. Patients with either a complete response (CR), partial response (PR), or hematologic improvement (HI) were considered as 'responders' (R, n=100, 47%), whereas patients described as having 'no response', 'stable disease', 'progressive disease', 'death' before response assessment, or 'not evaluable' were considered 'non-responders' (NR, n=133, 53%). Details of response rates by baseline characteristics and treatment types are shown in Table 2.

TABLE 2

Summary of Response vs. Pt. Characteristics and Treatment

| | Total | Non-Responders (NR/SD/PD/Died/NE) N (%) | Responders (CR/PR/HI) N (%) | p-value† |
|---|---|---|---|---|
| N, Total Treatment | 213 | 113 (53) | 100 (47) | |
| Azacitidine Alone | 42 (20) | 22 (52) | 20 (48) | 0.96 |
| Decitabine Alone | 144 (68) | 76 (53) | 68 (47) | |
| Decitabine+ | 27 (13) | 15 (56) | 12 (44) | |
| Sex | | | | |
| Male | 155 (73) | 82 (53) | 73 (47) | 0.99 |
| Female | 58 (27) | 31 (53) | 27 (47) | |
| Age | | | | |
| <70 yrs. | 110 (52) | 64 (58) | 46 (42) | 0.13 |
| ≥70 yrs. | 103 (48) | 49 (48) | 54 (52) | |
| FAB | | | | |
| RA | 30 (14) | 20 (67) | 10 (33) | 0.008† |
| RARS | 24 (11) | 15 (63) | 9 (38) | |
| RAEB | 125 (59) | 65 (52) | 60 (48) | |
| RAEB-t | 6 (3) | 4 (67) | 2 (33) | |
| CMML | 21 (10) | 4 (19) | 17 (81) | |
| Other | 7 (3) | 5 (71) | 2 (29) | |
| Risk Group | | | | |
| Low/Int-1 | 97 (46) | 53 (55) | 44 (45) | 0.78†† |
| Int-2/High | 113 (53) | 59 (52) | 54 (48) | |
| Unknown | 3 (1) | 1 (33) | 2 (67) | |
| Cytogenetics | | | | |
| Normal | 104 (49) | 49 (47) | 55 (53) | 0.13 |
| Other | 102 (48) | 59 (58) | 43 (42) | |
| Unknown | 7 (3) | 5 (71) | 2 (29) | |
| Complex | 51 (24) | 28 (55) | 23 (45) | 0.75 |
| Other | 155 (73) | 80 (52) | 75 (48) | |
| Unknown | 7 (3) | 5 (71) | 2 (29) | |

†Test included only known categories.
††No difference was observed between the 4 individual IPSS categories either (p = 0.24).

Sample Processing, DNA Sequencing, and Mutation Analysis:

DNA was extracted from bone marrow mononuclear cells or peripheral blood samples collected prior to transplant (median 18 days, range 9 to 119). Whole genome amplification of DNA for each sample was performed using the REPLI-g kit from Qiagen. A genotype fingerprint of 22 common single nucleotide polymorphisms (SNP) for each sample was generated by MALDI-TOF genotyping (Sequenom). Target regions of 40 genes and genotype fingerprint regions were enriched using Agilent SureSelect hybrid capture system according to manufacturer instructions. Barcoded samples were pooled in equimolar amounts and subjected to 100 nucleotide paired-end sequencing on an Illumina Hi Seq 2000. Sequence reads were aligned to the human genome (Build 37) using the Burroughs-Wheeler algorithm. The Genome Analysis Toolkit was used to clean and locally realign reads prior to calling missense and insertion/deletion variants using MuTect. Sample identity was confirmed by matching fingerprint genotype calls. Synonymous variants, non-coding variants more than 6 bases from splice junctions, or variants present in databases of "normal" genomes (dbSNP 132 or NHLBI Exome Sequencing Project) at a population frequency of 1% or more were discarded. Remaining variants were considered candidate somatic mutations.

Competitive Murine Bone Marrow Transplants:

Age-matched Tet2$^{-/-}$; Mx-Cre$^+$ and Tet2$^{+/+}$; Mx-Cre$^+$ donor animals (CD45.2) were treated with pIpC (15 µg/g IP) for three non-consecutive days to induce excision of exon 3 of Tet2. Donor bone marrow was harvested two weeks post-pIpC and mixed in a 1:2 ratio with bone marrow harvested from 45.1 WT donors (B6.SJL-Ptprca Pepcb/

BoyJ; Jackson), and was then transplanted into 45.1 recipients for a total of 1 million cells/recipient. Peripheral blood engraftment was assessed by FACS at two weeks post-transplant, at which point recipient mice were divided into treatment groups (n=7 per group) and treated with either 5-azacitidine (aza; 2.5 mg/kg IP; Santa Cruz Biotechnology) or vehicle control on the following schedule: two weeks on, two weeks off. Peripheral blood chimerism and CBC were assessed following each round of treatment. Percent 45.2 chimerism was calculated for each time point. Error bars indicate standard error of the mean (SEM) for each group, and p-values for the last time point were calculated using an unpaired two-sample t-test.

Statistical Methods:

Overall-survival (OS) was calculated from the date of transplant to the date of death, and surviving patients were censored at the date on which the patient was last known to be alive. Progression-free survival (PFS) was calculated from the time of transplant to the date of relapse, progression or death and was censored at the last date known alive and progression-free. Curves were constructed for OS and PFS using the method of Kaplan and Meier and compared using a log rank test. Cox models were constructed to adjust for clinical and transplant characteristics. A time-dependent variable for the interaction between mutation status and the natural log of time was also included in these models to test the proportional hazard assumption. Associations of continuous measures between groups were assessed using a Wilcoxon rank-sum test and for categorical variables were assessed using a Fisher exact test. P-values are two-sided and considered significant at the 0.05 level.

Results

Spectrum of Mutations

Tumor samples collected from 213 patients prior to treatment with AZA, DEC, or DEC+another agent were examined. Frequently mutated regions of 40 genes previously shown to be somatically mutated in patients with MDS were subject to hybrid capture and massively parallel sequencing. With this panel, one or more mutations were identified in several genes (FIG. 1). In total, 94% of patients had a mutation in at least one recurrently mutated gene. The most frequently mutated genes were ASXL1 (46%), TET2 (27%), RUNX1 (20%), TP53 (18%), and DNMT3A (16%) followed by the splicing factor genes SRSF2 (16%), SF3B1 (15%), and U2AF1 (14%) in which mutations were largely mutually exclusive.

Figure 2A:
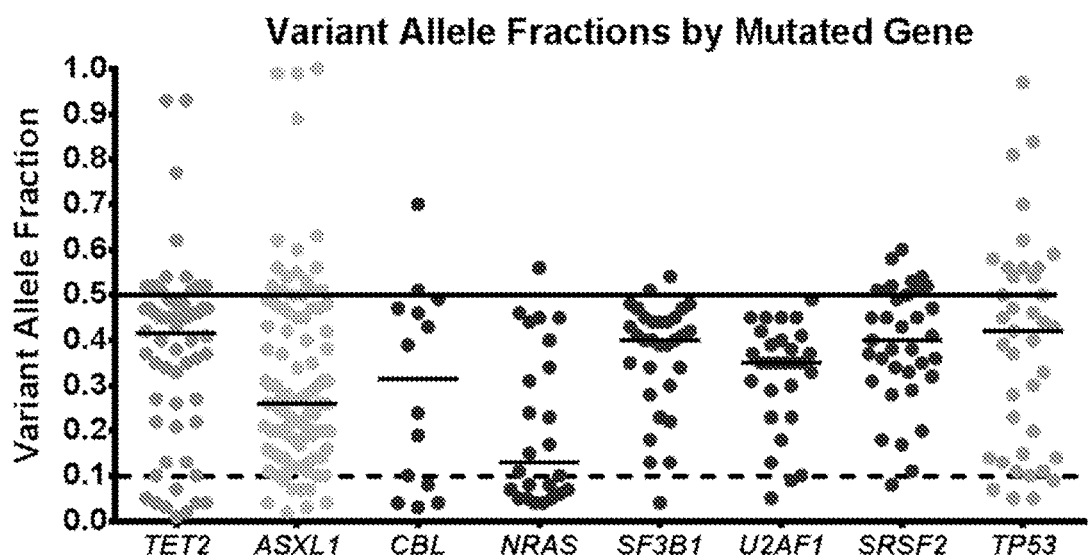
FIGS. 2A and 2B are a set of graphs showing variant Allele Frequencies in Selected Genes.
Figure 2B:
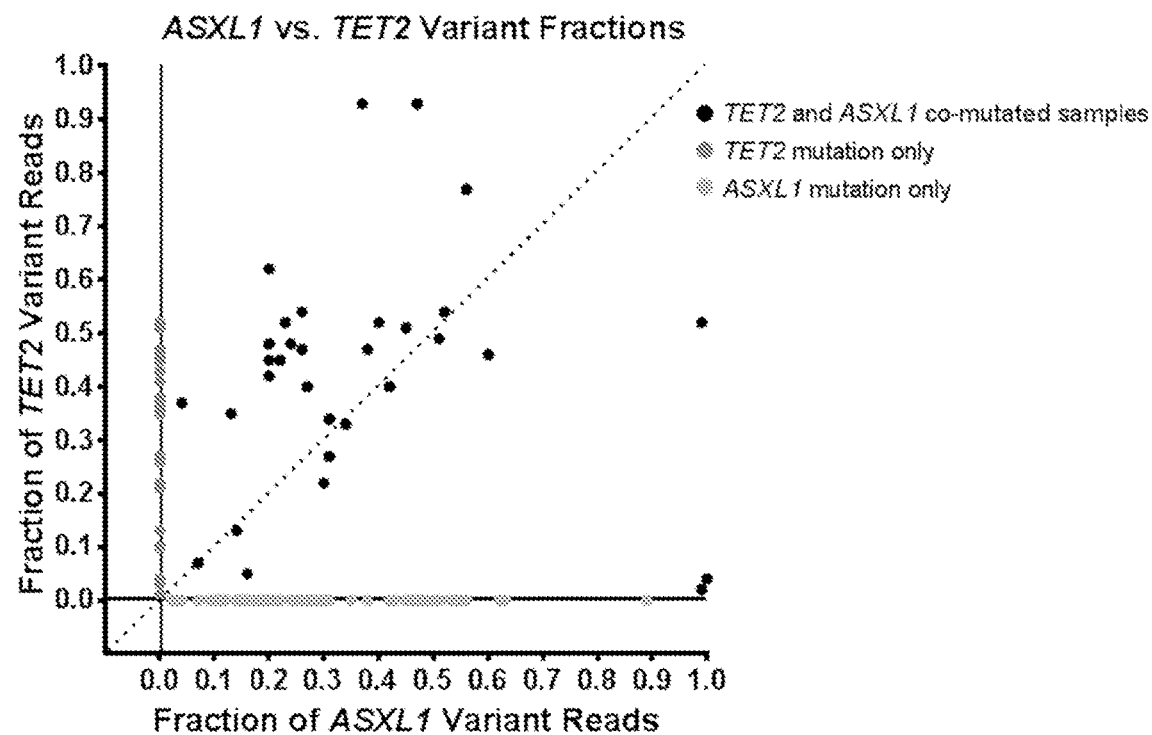

With the exception of ASXL1, the frequency of mutations identified in these genes was similar to those identified in other MDS patient cohorts. ASXL1 mutations were more frequent compared with prior studies that examined a higher proportion of lower risk patients, utilized less sensitive Sanger sequencing of ASXL1, excluded unannotated missense mutations, or excluded insertions in a homopolymeric tract near amino acid 642. Other previously observed patterns of mutations were identified in this cohort including the paucity of ASXL1 mutations in SF3B1 mutant samples, the mutual exclusivity of splicing factor mutations, and the decreased number of other gene mutations in patients with TP53 mutations. The mutations of TET2, ASXL1, NRAS, EZH2, and SRSF2 were overrepresented in CMML cases, SF3B1 mutations were predominantly in RARS cases, and mutations of TP53, IDH1, and IDH2 were relatively underrepresented in RA/RARS patients. The variant allele fractions (VAFs) for mutated genes were not uniform. Splicing factor abnormalities had a higher median variant allele fraction (VAF), while the VAFs for mutations in tyrosine kinase signaling genes were lower, indicative of their frequent presence in disease subclones (FIG. 2).

Clinical Findings, Variant Allele Fraction, and Response Rates

The overall response rate of patients in the study was 47% with 31% achieving a CR according to IWG criteria revised in 2006 (Table 2). There was no significant difference in response by treatment regimen or source of sample. IPSS risk groups and cytogenetic abnormalities were not predictive. The only clinical feature associated with response rate was FAB classification. Thirty-five percent of RA/RARS patients achieved a response compared with 47% of RAEB patients and 81% of CMML patients.

In the cohort in this study, TET2 mutant patients showed only a trend toward increased response rates (univariate OR 1.58, p=0.14). However, the VAF for mutations of TET2 and several other genes spanned a wide range of values including many likely to be below the detection limit for Sanger sequencing (FIG. 2). It was postulated that mutations capable of sensitizing cells to hypomethylating agents are more likely to be associated with a clinical response to treatment when they are present in a major disease clone. Similarly, mutations in genes that confer resistance to treatment may have no immediate effect if they occur only in a minor subclone. Therefore, mutations were examined with a VAF of 10% or greater (representing more than 20% of the sample cellularity in the case of heterozygous mutations). In this analysis, mutations of TET2 were associated with a significant increase in response rate (OR 1.99, p=0.036). This effect was most pronounced in the TET2 mutant, ASXL1 wildtype population (OR 3.65, p=0.011) which represented over 10% of patients in this cohort (Table 3).

TABLE 3

Mutations Associated with Response to Treatment

| Mutated Gene (n) | Unadjusted OR (95% CI) | p-value | Adjusted[†] OR (95% CI) | p-value |
| --- | --- | --- | --- | --- |
| Including, Only Mutations with VAF > 10% | | | | |
| TET2 mutant (50) | 1.99 (1.05, 3.80) | 0.036 | 1.98 (1.02, 3.85) | 0.044 |
| TET2 mutant + ASXL1 wt (23) | 3.65 (1.38, 9.67) | 0.009 | 3.64 (1.35, 9.79) | 0.011 |
| Including All Mutations | | | | |
| TET2 mutant (58) | 1.58 (0.86, 2.89) | 0.14 | 1.60 (0.85, 3.02) | 0.15 |
| TET2 mutant + ASXL1 wt (26) | 2.37 (1.00, 5.58) | 0.049 | 2.40 (0.99, 5.79) | 0.051 |
| CBL mutant (14) | 0.17 (0.04, 0.79) | 0.023 | 0.13 (0.03, 0.64) | 0.012 |
| NRAS mutant (24) | 2.04 (0.85, 4.89) | 0.11 | 2.67 (1.03, 6.93) | 0.043 |

[†]Adjusted for sex, age (<70, ≥70), IPSS (Low/Int1 vs. Int2/High)

No mutated genes were significantly associated with decreased rates of response in this analysis.

When all mutations were considered regardless of VAF, TET2 mutations alone were no longer predictive of response rate (HR 1.58, 95% CI 0.86-2.89), although TET2 mutant/ASXL1 wildtype patients retained their significant association with and increased response rate (HR 2.37, 95% CI 1.00-5.58). Only mutations of CBL, which were often of low VAF, were associated with a lower rate of response in this analysis (HR 0.17, 95% CI 0.04-0.79), but not when low VAF mutations were excluded.

In Vivo Model of Azacitidine Response in Tet2$^{-/-}$ Cells

Figure 3:
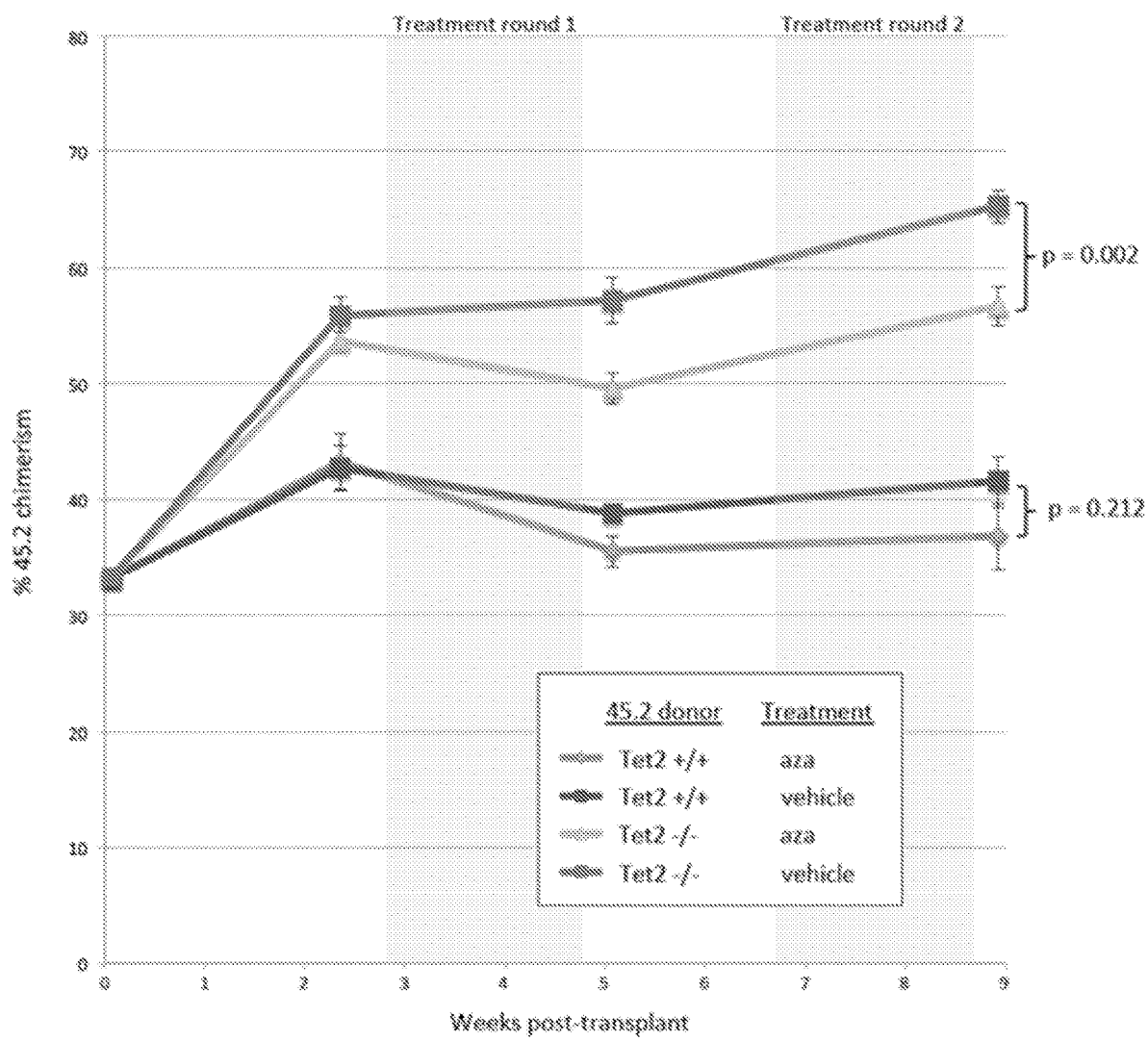
FIG. 3 is a Kaplan-Meier curve.

The observed association between TET2 mutations and response to treatment could be mediated directly by TET2 loss-of-function or by indirect or cell extrinsic effects. To test whether TET2 loss-of-function can sensitize cells to hypomethylating agents, we performed a competitive murine bone marrow transplant experiment using hematopoietic cells from Tet2-null and wildtype littermate donors. As expected, equal numbers of CD45.2$^+$ cells transplanted into CD45.1$^+$ recipients resulted in greater engraftment of Tet2-null cells at 2.5 weeks post-transplant. There was no difference in pretreatment peripheral blood counts between groups. Treatment with AZA (2.5 mg/kg M-F×2 weeks) or vehicle was begun on day 20 post-transplant and repeated starting on day 48. Regardless of genotype, azacitidine-treated animals exhibited significant decreases in WBC levels and hematocrit. After two cycles, AZA treated Tet2-null cells demonstrated a significantly decreased level of representation in peripheral blood while Tet2-wildtype cells did not (FIG. 3).

Associations with Overall Survival

Figure 4:
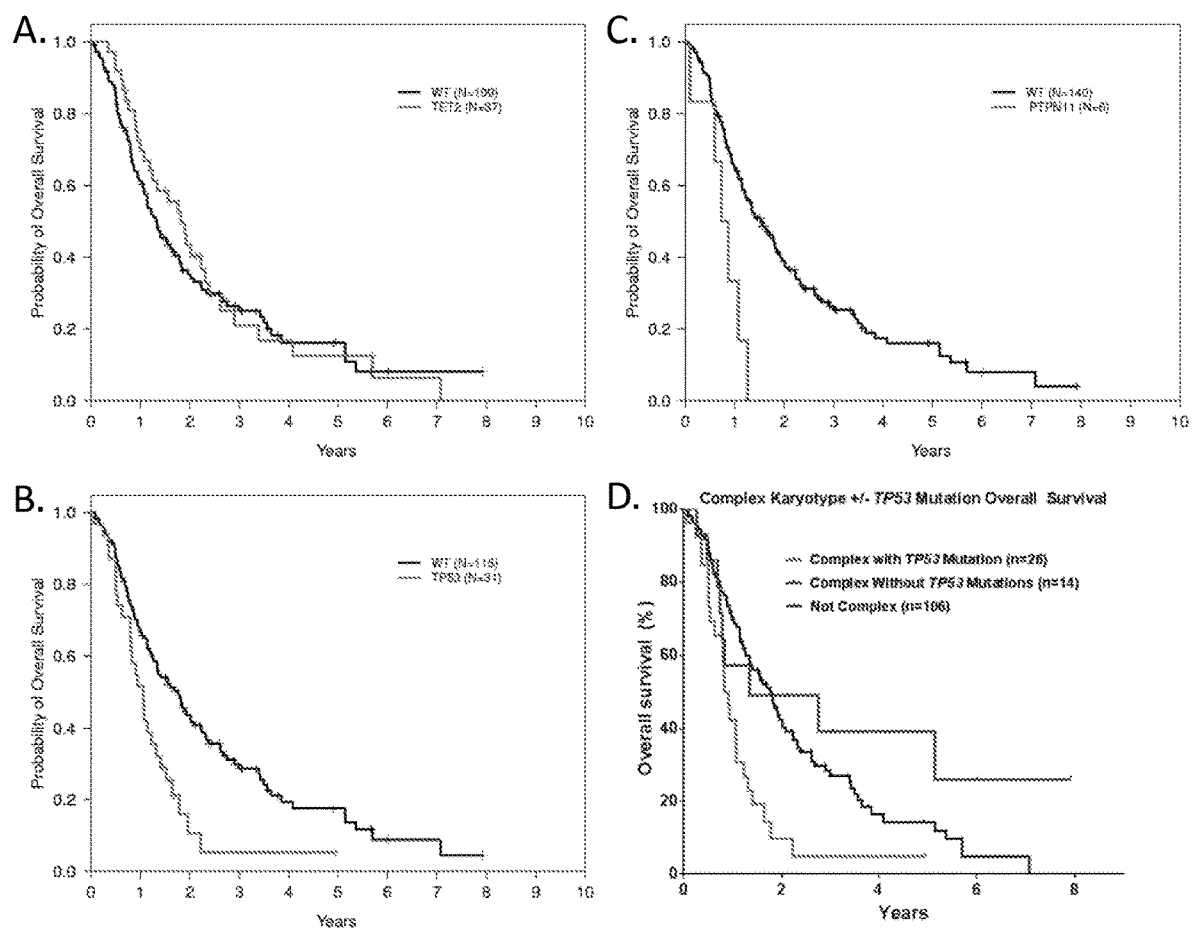
FIG. 4A-4C are a set of Kaplan-Meier curves for overall survival in the 146 out of 213 study patients with survival data FIG. 4A, Survival of patients with and without TET2 mutations.
FIG. 4D, Survival of complex karyotype patients with and without TP53 mutations vs. patients without complex karyotypes.
Figure 5:
FIG. 5 shows a schematic of a model of response in the case of mutations present in Tet2 and Asxl1.
Figure 5:
Figure 5:
Figure 5:
Figure 5:
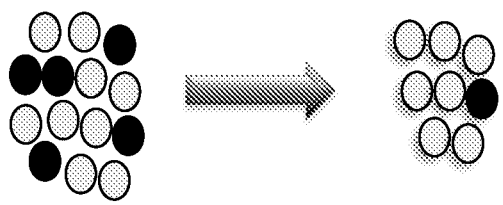
Figure 5:
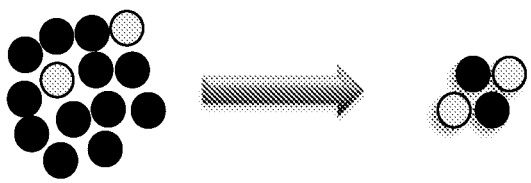
Figure 5:
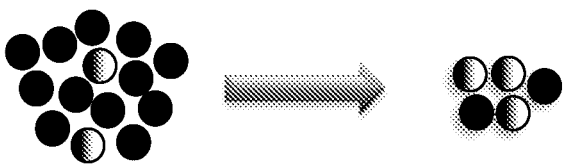
Figure 5:
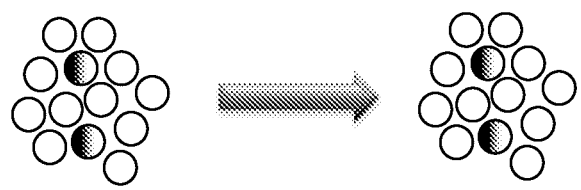
Figure 6:
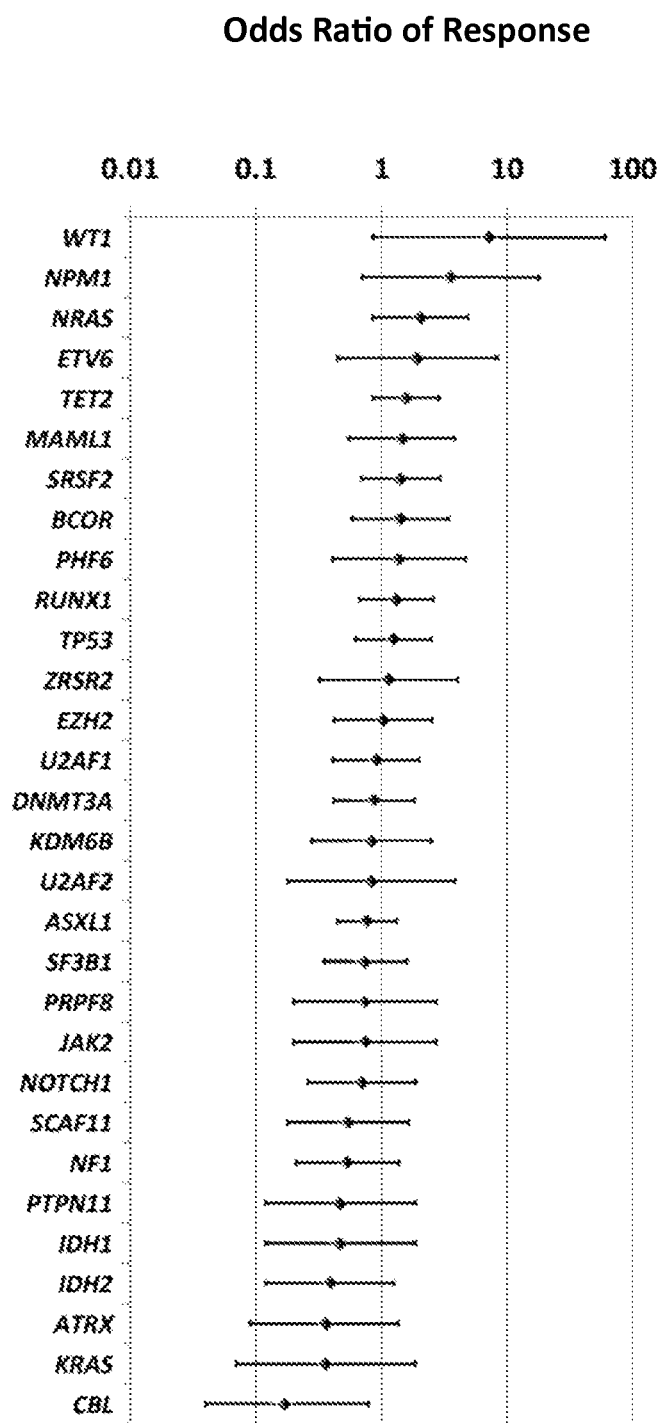
FIGS. 6 and 7 are additional supporting information.
Figure 7:
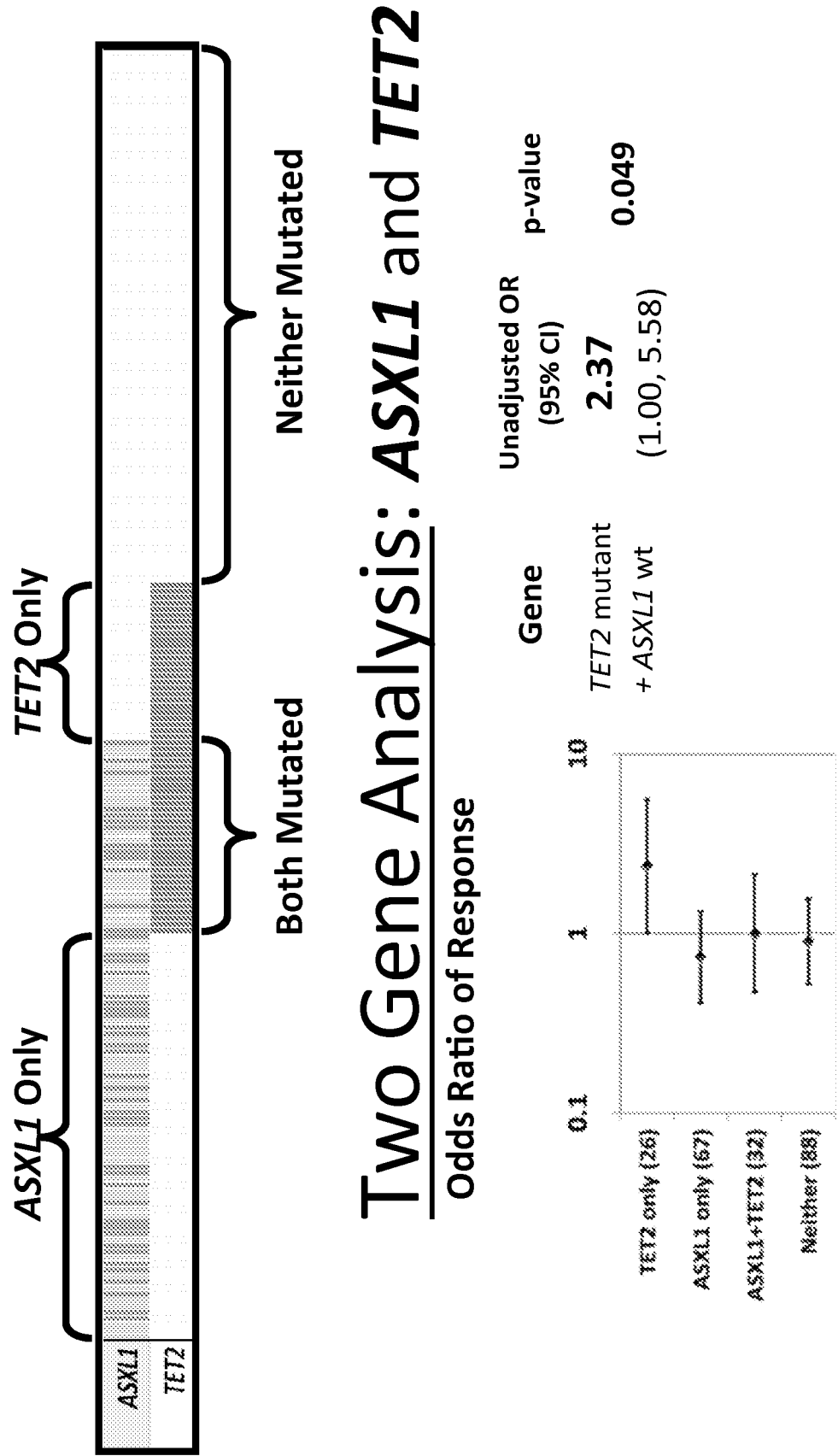

Traditional prognostic models like the IPSS and IPSS-R are based on patient cohorts examined only until they receive disease modifying therapies such as hypomethylating agents or undergo stem cell transplantation. Response to specific treatments could significantly alter the prognostic impact of adverse disease features or genetic alterations. The relationship between mutation status and survival was explored in the subset of patients for which we had long-term follow up. Survival data was available for 146 patients (69%) in our cohort of which 119 died. Multivariable COX modeling that considered patient age (<70 vs. >=70 yrs), sex, IPSS risk group (low/int1 vs. int-2/high), and all genes mutated in at least 5 patients identified only two mutated genes associated with overall survival. Despite its association with response, TET2 mutation status was not associated with overall survival, mirroring the finding in Itzykson et al (FIG. 4A). Mutation of TP53 was associated with decreased overall survival (21% of patients; HR 1.98, 95% CI 1.26-3.09; FIG. 4B) as were the rarer mutations of PTPN11 (4% of patients, HR 3.11, 95% CI 1.34-7.22; FIG. 4C).

Overall survival in patients with complex karyotypes was strongly associated with TP53 mutation status (FIG. 4D).

Discussion

In the studies presented herein, the presence of TET2 mutation at greater than 10% allele burden predicted an increased response to hypomethylating agents, particularly in the subset that lacked mutation of ASXL1. To achieve this result, tumor samples were examined from 213 MDS patients collected prior treatment with hypomethylating agents for mutations in 40 genes known to be recurrently mutated in MDS. The patients in this cohort were representative of those studied in clinical trials of AZA and DEC in terms of predicted disease risk and severity of cytopenias. Overall response rates were just under 50% and did not differ by the type of drug patients received. Using sensitive quantitative sequencing techniques, mutations were identifiable in over 90% of patients in patterns similar to those seen in prior multigene studies of MDS.

Itzykson et al. previously reported that 11 of 13 MDS patients with TET2 mutations detected by Sanger sequencing responded to treatment with AZA compared with a 52% response rate for their overall cohort of 86 patients. In this study, mutations in other genes were not examined and small subclonal TET2 mutations likely went undetected. As disclosed herein the broader and more sensitive multigene analysis also identified TET2 mutations as predictive of response to hypomethylating agents. Surprisingly, consideration of mutations in other genes did not discover additional biomarkers of response and inclusion of low VAF mutations weakened the association between TET2 mutation status and response rate. However, the approach disclosed herein identified the 10% of patients with mutated TET2 and wildtype ASXL1 as the group most likely to respond to treatment. Potential explanations for this finding include partial resistance to hypomethylating agents caused by ASXL1 mutations. In this model, the ASXL1 mutated subclone would be expected to grow in size during disease progression or relapse and might confer primary resistance. ASXL1 mutated patients with wildtype TET2 did have a lower likelihood of response, but this was not statistically significant (OR 0.63, 95% CI 0.34-1.16). Alternatively, it was observed that ASXL1 mutations were often subclonal or at a lower VAF than TET2 mutations in co-mutated patients (FIG. 2C). The acquisition of such secondary mutations (of which ASXL1 was the most frequent) could indicate more clonally progressive disease which may be inherently more resistant to treatment. However, no pattern of mutation was strongly associated with a lack of response to treatment.

The mechanism by which TET2 mutations might influence response to hypomethylating agents is not clear. Patients with TET2 mutations and animal models of Tet2 loss demonstrate elevated levels of DNA methylation in disease cells. However, measurement of pretreatment DNA methylation by itself is not predictive of response to hypomethylating agents. Similarly, cells with TET2 mutations are known to also have low-levels of 5-hydroxymethylated cytosines. Yet, many patients without TET2 mutations also have this epigenetic phenotype. It remains to be seen if these molecular features that are presumably downstream effects of somatic mutations might be better predictors of response either in isolation or in combination with clinical and genetic markers. In the murine bone marrow transplant experiment, exposure to AZA preferentially decreased the clonal advantage associated with loss of Tet2 function while increasing the total number of mature granulocytes. These effects may be associated with a greater AZA sensitivity in more actively cycling cells since AZA results in division-dependent passive demethylation of DNA. Mice with hematopoietic Tet2 loss are known to have increased myeloid progenitor proliferation whereas mice with Asxl1 loss have decreased stem cell self-renewal, consistent with the lower level of response we observed in TET2 mutant patients that also carried an ASXL1 mutation.

Over two-thirds of the cohort studied had sufficient follow-up to perform an overall survival analysis. Mutation profiles capable of predicting response to hypomethylating agents were not associated with differences in overall survival (FIG. 3). However, mutations in two genes that were not predictive of response, PTPN11 and TP53, were each associated with decreased overall survival. The presence of a complex karyotype is a known adverse risk factor and was associated with decreased overall survival in this cohort. More than half of the complex karyotype patients harbored a TP53 mutation (32/51) and these patients had a very short overall survival. However, complex karyotype patients without a detectable TP53 mutation had an overall survival that was no different from the group of patients with non-complex karyotypes. This indicates that the negative prognostic significance attributed the complex karyotype can be better explained by the TP53 mutation status of these patients. This finding has been identified in other MDS and AML patient populations, including a large cohort of mostly untreated MDS patients we reported on earlier. In that study, mutation in any of five genes, RUNX1, ASXL1, EZH2, ETV6, or TP53 were found to predict a shorter overall survival than expected by examining clinical features alone. Excepting TP53, mutations of these genes in this study population were not found to be prognostically adverse. This may be because the patients in the two studies are different, in that this cohort has more patients who are already higher risk based on clinical features. Alternatively, this could indicate that treatment with hypomethylating agents partially abrogates the adverse prognostic impact of these lesions. This would need to be validated in a larger independent cohort, but would form a justification for treating patients whose adverse prognosis is driven mutations in these genes.

The clinical implications of findings disclosed herein are that response to hypomethylating therapy can be predicted in a subset of patients using molecular genetic features.

Additional Statistical Methods

Categorical variables were compared using a Fisher exact test, while continuous variables were compared using a Wilcoxon rank-sum test. A Cochran-Mantel-Haenszel (CMH) test was used to test for differences in response rate by mutational status controlling for treatment. Unadjusted and adjusted logistic regression models were used to predict response to therapy. A stepwise algorithm for logistic regression was also utilized to determine a final model; candidate variables considered for inclusion were all mutations, treatment, IPSS classification, age, and sex. The Hosmer and Lemeshow goodness-of-fit test was used to assess model fit for logistic regression models. Overall survival was calculated from the time of treatment to the time of death from any cause or was censored at the date last known alive. Unadjusted and adjusted Cox regression models were constructed for overall survival. A stepwise regression algorithm for Cox regression models was used including the same candidate variables as in the logistic regression modeling. Classification trees were also created using the Rpart package in R version 2.11.1 to classify responders based on mutational status. Cross-validation was used for tree pruning. All p-values reported are two-sided and considered significant at the 0.05 level. No adjustments were made for multiple hypothesis testing.

TABLE 3

Patient Characteristics/Mutational Distribution Comparison Between Cohorts

|  | NEJM | Hypo All | Hypo with Survival |
|---|---|---|---|
| No. of Pts | 439 | 213 | 146 |
| Age, median (range) | 70 (15, 91) | 69 (31, 89) | 67 (31, 89) |
| Sex, M | 306 (70) | 155 (73) | 107 (73) |
| IPSS |  |  |  |
| Low | 110 (25) | 11 (5) | 10 (7) |
| Intermediate 1 | 185 (42) | 86 (40) | 47 (32) |
| Intermediate 2 | 101 (23) | 76 (36) | 65 (45) |
| High | 32 (7) | 37 (1) | 22 (15) |
| Unknown | 11 (3) | 3 (1) | 2 (1) |
| Mutation Type†† |  |  |  |
| TET2 | 90 (21) | 58 (27) | 37 (25) |
| ASXL1 | 63 (14) | 99 (46) | 71 (49) |
| RUNX1 | 38 (9) | 42 (20) | 27 (18) |
| TP53 | 33 (8) | 39 (18) | 31 (21) |
| EZH2 | 28 (6) | 21 (10) | 12 (8) |
| NRAS | 16 (4) | 24 (11) | 17 (12) |
| JAK2 | 13 (3) | 10 (5) | 9 (6) |
| ETV6 | 12 (3) | 8 (4) | 3 (2) |
| CBL | 10 (2) | 14 (7) | 8 (5) |
| IDH2 | 9 (2) | 15 (7) | 11 (8) |
| NPM1 | 8 (2) | 8 (4) | 6 (4) |
| IDH1 | 6 (1) | 10 (5) | 8 (5) |
| KRAS | 4 (1) | 8 (4) | 5 (3) |
| GNAS | 3 (<1) | 1 (<1) | 1 (<1) |

TABLE 3-continued

Patient Characteristics/Mutational Distribution Comparison Between Cohorts

|  | NEJM | Hypo All | Hypo with Survival |
|---|---|---|---|
| PTPN11 | 3 (<1) | 10 (5) | 6 (4) |
| BRAF | 2 (<1) | 1 (<1) | 0 (0) |
| PTEN | 1 (<1) | 0 (0) | 0 (0) |
| CDKN2A | 1 (<1) | 0 (0) | 0 (0) |

TABLE 5

Response Summary

|  | N (%) |
|---|---|
| N | 213 |
| Response |  |
| CR | 67 (31) |
| PR | 5 (2) |
| HI | 28 (13) |
| SD | 34 (16) |
| NR | 46 (22) |
| PD/Died | 23 (11) |
| NE | 10 (5) |
| Responders (CR/PR/HI) | 100 (47) |
| Non-Responders | 113 (53) |

TABLE 6

Summary of CBL Mutations vs. Pt. Characteristics and Treatment

|  | No CBL Mutation N (%) | CBL Mutation N (%) | p-value† |
|---|---|---|---|
| N, Total | 199 | 14 |  |
| Treatment |  |  |  |
| Aza Alone | 38 (19) | 4 (29) | 0.69 |
| Decitabine Alone | 135 (68) | 9 (64) |  |
| Decitabine + Other | 26 (13) | 1 (7) |  |
| Sex |  |  |  |
| Male | 145 (73) | 10 (71) | 0.99 |
| Female | 54 (27) | 4 (29) |  |
| Age |  |  |  |
| <70 yrs. | 101 (51) | 9 (64) | 0.41 |
| ≥70 yrs. | 98 (49) | 5 (36) |  |
| FAB |  |  |  |
| RA | 29 (15) | 1 (7) | 0.92 |
| RARS | 22 (11) | 2 (14) |  |
| RAEB | 115 (58) | 10 (71) |  |
| RAEB-t | 6 (3) | 0 (0) |  |
| CMML | 20 (10) | 1 (7) |  |
| Other | 7 (4) | 0 (0) |  |
| Risk Group |  |  |  |
| Low/Int-1 | 90 (45) | 7 (50) | 0.78†† |
| Int-2/High | 106 (53) | 7 (50) |  |
| Unknown | 3 (2) | 0 (0) |  |
| Cytogenetics |  |  |  |
| Normal | 96 (48) | 8 (57) | 0.57 |
| Other | 97 (49) | 5 (36) |  |
| Unknown | 6 (3) | 1 (7) |  |

†Test included only known categories.
††No difference was observed between 4 categories either (p = 0.24).

TABLE 7

Mutation Status vs. Response Rate for each Treatment (Mutations ≥4% test)

| Gene | No. of Mutations (%) | Overall Response N (%) | Aza Alone Response N (%) | Dec Alone Response N (%) | Dec Plus Response N (%) | p-value† |
|---|---|---|---|---|---|---|
| N | | 113 | 42 | 144 | 27 | |
| Responses | | 100 (47) | 20 (48) | 68 (47) | 12 (44) | 0.96 |
| ASXL1 | 99 (46) | 43 (43) | 11 (46) | 29 (42) | 3 (50) | 0.30 |
| TET2 | 58 (27) | 32 (55) | 6 (50) | 22 (54) | 4 (80) | 0.15 |
| RUNX1 | 42 (20) | 22 (52) | 3 (38) | 16 (53) | 3 (75) | 0.44 |
| TP53 | 39 (18) | 20 (51) | 6 (75) | 9 (47) | 5 (42) | 0.49 |
| SRSF2 | 35 (16) | 19 (54) | 3 (50) | 14 (56) | 2 (50) | 0.35 |
| DNMT3A | 34 (16) | 15 (44) | 3 (50) | 8 (36) | 4 (67) | 0.73 |
| SF3B1 | 32 (15) | 13 (41) | 3 (50) | 8 (36) | 2 (50) | 0.44 |
| U2AF1 | 29 (14) | 13 (45) | 4 (40) | 9 (50) | 0 (0) | 0.78 |
| NOTCH2 | 28 (13) | 18 (64) | 2 (50) | 11 (58) | 5 (100) | 0.047 |
| NRAS | 24 (11) | 15 (63) | 3 (43) | 11 (73) | 1 (50) | 0.11 |
| BCOR | 22 (10) | 12 (55) | 2 (50) | 9 (56) | 1 (50) | 0.46 |
| NF1 | 21 (10) | 7 (33) | 2 (33) | 4 (31) | 1 (50) | 0.19 |
| EZH2 | 21 (10) | 10 (48) | 3 (75) | 7 (44) | 0 (0) | 0.97 |
| MAML1 | 18 (8) | 10 (56) | 0 (0) | 7 (54) | 3 (75) | 0.43 |
| NOTCH1 | 18 (8) | 7 (39) | 2 (67) | 5 (38) | 0 (0) | 0.48 |
| IDH2 | 15 (7) | 4 (27) | 2 (67) | 2 (17) | 0 (0) | 0.097 |
| SCAF11 | 15 (7) | 5 (33) | 1 (20) | 2 (25) | 2 (100) | 0.27 |
| KDM6B | 14 (7) | 6 (43) | 1 (33) | 2 (25) | 3 (100) | 0.77 |
| CBL | 14 (7) | 2 (14) | 1 (25) | 1 (11) | 0 (0) | 0.011 |
| TLR1 | 13 (6) | 7 (54) | 0 (0) | 5 (71) | 2 (67) | 0.59 |
| ATRX | 12 (6) | 3 (25) | 0 (0) | 2 (25) | 1 (100) | 0.12 |
| KDM3A | 11 (5) | 2 (18) | 0 (0) | 2 (25) | 0 (0) | 0.052 |
| PHF6 | 11 (5) | 6 (55) | 1 (100) | 5 (50) | 0 (0) | 0.62 |
| PRPF8 | 10 (5) | 4 (40) | 1 (100) | 3 (33) | 0 (0) | 0.64 |
| PTPN11 | 10 (5) | 3 (30) | 0 (0) | 1 (17) | 2 (67) | 0.29 |
| ZRSR2 | 10 (5) | 5 (50) | 1 (100) | 4 (44) | 0 (0) | 0.86 |
| IDH1 | 10 (5) | 3 (30) | 1 (50) | 2 (25) | 0 (0) | 0.26 |
| JAK2 | 10 (5) | 4 (40) | 2 (100) | 2 (40) | 0 (0) | 0.68 |
| KRAS | 8 (4) | 2 (25) | 1 (50) | 1 (20) | 0 (0) | 0.21 |
| NPM1 | 8 (4) | 6 (75) | 0 (0) | 5 (71) | 1 (100) | 0.10 |
| ETV6 | 8 (4) | 5 (63) | 2 (100) | 3 (50) | 0 (0) | 0.38 |

†Cochran-Mantel-Haenszel (CMH) test for all but the 1st comparison which used a Fisher exact test

TABLE 8

Mutation Status vs. Response Rate for each Treatment (Mutations ≥4% test)

| Gene | No. of Mutations (%) | Overall Response N (%) | Aza Alone Response N (%) | Dec +/− Response N (%) | p-value† |
|---|---|---|---|---|---|
| N | | 113 | 42 | 171 | |
| Responses | | 100 (47) | 20 (48) | | |
| ASXL1 | 99 (46) | 43 (43) | 11 (46) | 32 (43) | 0.33 |
| TET2 | 58 (27) | 32 (55) | 6 (50) | 26 (57) | 0.14 |
| RUNX1 | 42 (20) | 22 (52) | 3 (38) | 19 (56) | 0.43 |
| TP53 | 39 (18) | 20 (51) | 6 (75) | 14 (45) | 0.55 |
| SRSF2 | 35 (16) | 19 (54) | 3 (50) | 16 (55) | 0.34 |
| DNMT3A | 34 (16) | 15 (44) | 3 (50) | 12 (43) | 0.72 |
| SF3B1 | 32 (15) | 13 (41) | 3 (50) | 10 (38) | 0.44 |
| U2AF1 | 29 (14) | 13 (45) | 4 (40) | 9 (47) | 0.79 |
| NOTCH2 | 28 (13) | 18 (64) | 2 (50) | 16 (67) | 0.049 |
| NRAS | 24 (11) | 15 (63) | 3 (43) | 12 (71) | 0.11 |
| BCOR | 22 (10) | 12 (55) | 2 (50) | 10 (56) | 0.45 |
| NF1 | 21 (10) | 7 (33) | 2 (33) | 5 (33) | 0.19 |
| EZH2 | 21 (10) | 10 (48) | 3 (75) | 7 (41) | 0.95 |
| MAML1 | 18 (8) | 10 (56) | 0 (0) | 10 (59) | 0.44 |
| NOTCH1 | 18 (8) | 7 (39) | 2 (67) | 5 (33) | 0.48 |
| IDH2 | 15 (7) | 4 (27) | 2 (67) | 2 (17) | 0.10 |
| SCAF11 | 15 (7) | 5 (33) | 1 (20) | 4 (40) | 0.27 |
| KDM6B | 14 (7) | 6 (43) | 1 (33) | 5 (45) | 0.75 |
| CBL | 14 (7) | 2 (14) | 1 (25) | 1 (10) | 0.011 |
| TLR1 | 13 (6) | 7 (54) | 0 (0) | 7 (70) | 0.61 |
| ATRX | 12 (6) | 3 (25) | 0 (0) | 3 (33) | 0.12 |
| KDM3A | 11 (5) | 2 (18) | 0 (0) | 2 (20) | 0.051 |
| PHF6 | 11 (5) | 6 (55) | 1 (100) | 5 (50) | 0.60 |
| PRPF8 | 10 (5) | 4 (40) | 1 (100) | 3 (33) | 0.66 |
| PTPN11 | 10 (5) | 3 (30) | 0 (0) | 3 (33) | 0.27 |
| ZRSR2 | 10 (5) | 5 (50) | 1 (100) | 4 (44) | 0.84 |
| IDH1 | 10 (5) | 3 (30) | 1 (50) | 2 (25) | 0.27 |
| JAK2 | 10 (5) | 4 (40) | 2 (100) | 2 (25) | 0.65 |
| KRAS | 8 (4) | 2 (25) | 1 (50) | 1 (17) | 0.21 |
| NPM1 | 8 (4) | 6 (75) | 0 (0) | 6 (75) | 0.10 |
| ETV6 | 8 (4) | 5 (63) | 2 (100) | 3 (50) | 0.37 |

†Cochran-Mantel-Haenszel (CMH) test for all but the 1st comparison which used a Fisher exact test

TABLE 9

Time to Best Response for 47 MD Anderson Responders (CR/PR/HI)
Note the median time to best response for al 47 pts was
3.0 months range (0.9, 18.8) and only those with 4 or
more mutations of the 47 pts are presented.

| Gene | N No Mutation | Time to Response (months) No Mutation median (range)† | N Mutation | Time to Response (months) Mutation Present median (range)† | p-value†† |
|---|---|---|---|---|---|
| ASXL1 | 24 | 2.4 (0.9, 18.8) | 23 | 3.2 (0.9, 13.6) | 0.091 |
| TET2 | 31 | 3.1 (0.9, 13.6) | 16 | 3.0 (0.9, 18.8) | 0.80 |
| RUNX1 | 36 | 2.9 (0.9, 18.8) | 11 | 4.0 (0.9, 13.6) | 0.072 |
| TP53 | 34 | 3.2 (0.9, 18.8) | 13 | 2.9 (1.4, 6.8) | 0.58 |
| SRSF2 | 37 | 3.1 (0.9, 18.8) | 10 | 2.9 (0.9, 9.7) | 0.70 |
| DNMT3A | 38 | 3.0 (0.9, 18.8) | 9 | 3.8 (1.0, 9.7) | 0.30 |
| SF3B1 | 42 | 3.0 (1.0, 18.8) | 5 | 3.8 (1.0, 5.9) | 0.90 |
| U2AF1 | 41 | 2.9 (0.9, 18.8) | 6 | 4.7 (0.9, 13.6) | 0.21 |
| NOTCH2 | 38 | 3.1 (0.9, 13.6) | 9 | 3.0 (1.0, 18.8) | 0.81 |
| NRAS | 40 | 3.1 (0.9, 18.8) | 7 | 2.9 (0.9, 9.9) | 0.89 |
| BCOR | 43 | 3.0 (0.9, 18.8) | 4 | 5.8 (1.0, 9.7) | 0.21 |
| NF1 | 43 | 3.0 (0.9, 13.6) | 4 | 3.9 (1.7, 18.8) | 0.35 |
| EZH2 | 43 | 3.0 (0.9, 18.8) | 4 | 3.5 (0.9, 9.9) | 0.75 |
| MAML1 | 42 | 3.1 (0.9, 18.8) | 5 | 2.4 (0.9, 6.2) | 0.81 |

†Calculated from the date of treatment note only MD Anderson pts had dates of best response
††Wilcoxon rank-sum test

TABLE 10

146 Patients with Outcome Data (non-Daco trial pts) (≥3%; 5 or more muts)

| Gene with Mutation | N Pts w/a Mutation (%) | Univariate† HR (95% CI) | p-value† | IPSS and Treatment Adjusted† HR (95% CI) | p-value† |
|---|---|---|---|---|---|
| N pts | 146 | | | | |
| ASXL1 | 71 (49) | 1.12 (0.77-1.61) | 0.56 | 1.18 (0.81-1.71) | 0.40 |
| TET2 | 37 (25) | 0.88 (0.58-1.34) | 0.56 | 0.93 (0.61-1.42) | 0.74 |
| RUNX1 | 27 (18) | 1.04 (0.66-1.65) | 0.86 | 0.97 (0.61-1.55) | 0.90 |
| TP53 | 31 (21) | 2.01 (1.29-3.14) | 0.002 | 1.91 (1.20-3.05) | 0.007 |
| SRSF2 | 26 (18) | 1.03 (0.65-1.63) | 0.90 | 1.05 (0.66-1.67) | 0.84 |
| DNMT3A | 26 (18) | 0.97 (0.61-1.54) | 0.90 | 0.78 (0.48-1.27) | 0.32 |
| SF3B1 | 17 (12) | 1.02 (0.57-1.83) | 0.94 | 0.96 (0.53-1.73) | 0.89 |
| U2AF1 | 23 (16) | 1.08 (0.65-1.79) | 0.76 | 1.17 (0.70-1.95) | 0.56 |
| NOTCH2 | 18 (12) | 0.67 (0.38-1.21) | 0.18 | 0.65 (0.36-1.16) | 0.14 |
| NRAS | 17 (12) | 1.02 (0.58-1.79) | 0.94 | 1.01 (0.57-1.77) | 0.98 |
| BCOR | 13 (9) | 1.17 (0.63-2.19) | 0.62 | 1.07 (0.57-2.02) | 0.82 |
| NF1 | 16 (11) | 0.93 (0.50-1.74) | 0.82 | 1.00 (0.52-1.94) | 0.99 |
| EZH2 | 12 (8) | 1.24 (0.64-2.37) | 0.52 | 1.57 (0.79-3.09) | 0.20 |
| MAML1 | 10 (7) | 1.37 (0.72-2.63) | 0.34 | 1.31 (0.68-2.54) | 0.43 |
| NOTCH1 | 12 (8) | 0.64 (0.31-1.34) | 0.24 | 0.70 (0.33-1.48) | 0.34 |
| IDH2 | 11 (8) | 1.69 (0.88-3.26) | 0.11 | 1.84 (0.94-3.58) | 0.075 |
| SCAF11 | 12 (8) | 1.12 (0.59-2.15) | 0.73 | 1.01 (0.52-1.99) | 0.97 |
| KDM6B | 9 (6) | 0.84 (0.39-1.80) | 0.65 | 0.71 (0.32-1.55) | 0.38 |
| CBL | 8 (5) | 1.07 (0.50-2.30) | 0.86 | 1.04 (0.48-2.27) | 0.91 |
| TLR1 | 10 (7) | 1.08 (0.52-2.21) | 0.84 | 1.04 (0.51-2.14) | 0.92 |
| ATRX | 8 (5) | 1.12 (0.49-2.55) | 0.80 | 1.19 (0.51-2.77) | 0.68 |
| KDM3A | 7 (5) | 1.20 (0.56-2.59) | 0.64 | 1.17 (0.54-2.55) | 0.69 |
| PHF6 | 5 (3) | 0.81 (0.30-2.20) | 0.68 | 0.79 (0.28-2.20) | 0.65 |
| PRPF8 | 6 (4) | 1.72 (0.75-3.94) | 0.20 | 2.00 (0.86-4.66) | 0.11 |
| PTPN11 | 6 (4) | 3.26 (1.41-7.58) | 0.006 | 2.47 (0.98-6.26) | 0.056 |
| IDH1 | 8 (5) | 1.11 (0.51-2.38) | 0.80 | 1.15 (0.52-2.51) | 0.73 |
| JAK2 | 9 (6) | 0.65 (0.30-1.43) | 0.28 | 0.65 (0.29-1.44) | 0.28 |
| KRAS | 5 (3) | 0.98 (0.31-3.09) | 0.97 | 1.72 (0.53-5.63) | 0.37 |
| NPM1 | 6 (4) | 0.77 (0.28-2.09) | 0.61 | 0.80 (0.29-2.19) | 0.66 |
| TLR6 | 7 (5) | 1.10 (0.45-2.70) | 0.84 | 1.08 (0.44-2.66) | 0.87 |
| MYBL2 | 5 (3) | 0.87 (0.32-2.37) | 0.79 | 0.97 (0.35-2.68) | 0.95 |

†Compared to group without that mutation
††Adjusted for IPSS and treatment excludes 2 pts with unknown IPSS

TABLE 11

Final Cox Regression Model from Stepwise Procedure. Candidate
variables included age (<70 vs. >=70 yrs), sex, IPSS
(low/int1 vs. int-2/high), and all mutations (≥3%; 5 or more muts)

| Gene | Adjusted HR† (95% CI) | p-value |
|---|---|---|
| TP53 | 2.30 (1.45, 3.67) | <0.001 |
| PTPN11 | 4.48 (1.84, 10.91) | <0.001 |
| NOTCH2 | 0.47 (0.25, 0.87) | 0.017 |

TABLE 12

Final Cox Regression Model from Stepwise Procedure. Candidate
variables included age (<70 vs. >=70 yrs), sex,
IPSS (low/int1 vs. int-2/high), and all mutations (≥3%;
5 or more muts) NO NOTCH2 OR NOTCH1 as candidates

| Gene | Adjusted HR† (95% CI) | p-value |
|---|---|---|
| TP53 | 1.98 (1.26, 3.09) | 0.003 |
| PTPN11 | 3.11 (1.34, 7.22) | 0.008 |

TABLE 13

Number of Mutations for Combinations of ASXL1 vs. TET2 for those with Survival Data

| Gene | N Mutations (%) |
|---|---|
| N pts | 146 |
| ASXL1 | 71 (49) |
| TET2 | 37 (25) |
| ASXL1 wt + TET2 | 26 (12) |
| ASXL1 + TET2 wt | 67 (31) |
| ASXL1 + TET2 | 32 (15) |
| No ASXL1 or TET2 | 88 (41) |

TABLE 14

Univariate Cox Regression Models for OS for 146 Patients (non-Daco trial pts) Comparing Combinations of ASXL1 and TET2

| Gene | Univariate† HR (95% CI) | p-value |
|---|---|---|
| N pts | 146 | |
| ASXL1 | 1.12 (0.77-1.61) | 0.56 |
| TET2 | 0.88 (0.58-1.34) | 0.56 |
| ASXL1 wt + TET2 | 0.70 (0.37-1.30) | 0.26 |
| ASXL1 + TET2 wt | 1.08 (0.73-1.59) | 0.71 |
| ASXL1 + TET2 | 1.09 (0.66-1.78) | 0.74 |
| No ASXL1 or TET2 | 1.04 (0.71-1.51) | 0.85 |

Excluding Mutations with Mutant Allele Frequency <0.10

TABLE 15

Excluding Mutations with Mutant Allele Frequency <0.10
Response Rate versus Mutational Status Logistic Regression (modeling the probability of response) adjusted models include age (>=70 yrs. vs. <70), sex, IPSS (low/int-1 vs. int-2/high) and treatment
Note: Higher OR indicates a higher probability of response (OR > 1) whereas lower OR indicates response less likely with the mutation.

| Gene (vs. WT for OR) | N Mutations (%) | N (%) Response | Unadjusted OR (95% CI) | p-value | Adjusted OR† (95% CI) | p-value |
|---|---|---|---|---|---|---|
| ASXL1 | 91 (43) | 38 (42) | 0.69 (0.40, 1.20) | 0.19 | 0.68 (0.38, 1.19) | 0.17 |
| TET2 | 50 (23) | 30 (60) | 1.99 (1.05, 3.80) | 0.036 | 1.98 (1.02, 3.85) | 0.044 |
| RUNX1 | 38 (18) | 20 (53) | 1.32 (0.65, 2.67) | 0.44 | 1.28 (0.63, 2.61) | 0.50 |
| TP53 | 35 (16) | 16 (46) | 0.94 (0.46, 1.95) | 0.87 | 0.86 (0.39, 1.90) | 0.72 |
| SRSF2 | 34 (16) | 18 (53) | 1.33 (0.64, 2.78) | 0.45 | 1.34 (0.63, 2.82) | 0.45 |
| DNMT3A | 30 (14) | 13 (43) | 0.84 (0.39, 1.84) | 0.67 | 0.88 (0.39, 1.98) | 0.76 |
| SF3B1 | 31 (15) | 12 (39) | 0.68 (0.31, 1.47) | 0.32 | 0.61 (0.26, 1.40) | 0.24 |
| U2AF1 | 27 (13) | 12 (44) | 0.89 (0.40, 2.01) | 0.78 | 0.87 (0.37, 2.01) | 0.74 |
| NOTCH2 | 26 (12) | 17 (65) | 2.37 (1.00, 5.58) | 0.049 | 2.61 (1.08, 6.29) | 0.032 |
| NRAS | 14 (7) | 10 (71) | 3.03 (0.92, 9.97) | 0.069 | 2.97 (0.88, 9.98) | 0.079 |
| BCOR | 20 (9) | 11 (55) | 1.43 (0.57, 3.60) | 0.45 | 1.44 (0.56, 3.70) | 0.45 |
| NF1 | 16 (8) | 6 (38) | 0.66 (0.23, 1.88) | 0.43 | 0.60 (0.20, 1.86) | 0.38 |
| EZH2 | 20 (9) | 9 (45) | 0.92 (0.36, 2.31) | 0.85 | 0.84 (0.32, 2.18) | 0.72 |
| MAML1 | 17 (8) | 10 (59) | 1.68 (0.62, 4.60) | 0.31 | 1.53 (0.54, 4.31) | 0.42 |
| NOTCH1 | 18 (8) | 7 (39) | 0.70 (0.26, 1.88) | 0.48 | 0.63 (0.23, 1.72) | 0.36 |
| IDH2 | 9 (4) | 3 (33) | 0.55 (0.13, 2.27) | 0.41 | 0.58 (0.14, 2.43) | 0.46 |
| SCAF11 | 14 (7) | 5 (36) | 0.61 (0.20, 1.88) | 0.39 | 0.60 (0.19, 1.90) | 0.39 |
| KDM6B | 12 (6) | 6 (50) | 1.14 (0.36, 3.65) | 0.83 | 1.09 (0.33, 3.58) | 0.88 |
| CBL | 10 (5) | 2 (20) | 0.27 (0.06, 1.29) | 0.10 | 0.28 (0.06, 1.40) | 0.12 |
| TLR1 | 12 (6) | 6 (50) | 1.14 (0.36, 3.65) | 0.83 | 1.31 (0.40, 4.30) | 0.66 |
| ATRX | 7 (3) | 1 (14) | 0.18 (0.02, 1.52) | 0.12 | 0.15 (0.02, 1.32) | 0.087 |
| KDM3A | 8 (4) | 1 (13) | 0.15 (0.02, 1.27) | 0.082 | 0.15 (0.02, 1.29) | 0.084 |
| PHF6 | 8 (4) | 5 (63) | 1.93 (0.45, 8.29) | 0.38 | 1.72 (0.38, 7.77) | 0.48 |
| PRPF8 | 7 (3) | 2 (29) | 0.44 (0.08, 2.33) | 0.33 | 0.40 (0.07, 2.17) | 0.29 |
| PTPN11 | 2 (1) | 1 (50) | 1.13 (0.07, 18.33) | 0.93 | 1.42 (0.08, 24.43) | 0.81 |

TABLE 15-continued

Excluding Mutations with Mutant Allele Frequency <0.10
Response Rate versus Mutational Status Logistic Regression (modeling
the probability of response) adjusted models include age (>=70 yrs.
vs. <70), sex, IPSS (low/int-1 vs. int-2/high) and treatment
Note: Higher OR indicates a higher probability of response (OR > 1)
whereas lower OR indicates response less likely with the mutation.

| Gene (vs. WT for OR) | N Mutations (%) | N (%) Response | Unadjusted OR (95% CI) | p-value | Adjusted OR† (95% CI) | p-value |
|---|---|---|---|---|---|---|
| ZRSR2 | 8 (4) | 4 (50) | 1.14 (0.28, 4.67) | 0.86 | 1.13 (0.26, 4.85) | 0.87 |
| IDH1 | 8 (4) | 3 (38) | 0.67 (0.16, 2.87) | 0.59 | 0.66 (0.15, 2.85) | 0.57 |
| JAK2 | 8 (4) | 3 (38) | 0.67 (0.16, 2.87) | 0.59 | 0.69 (0.16, 3.00) | 0.62 |
| KRAS | 6 (3) | 2 (33) | 0.56 (0.10, 3.10) | 0.50 | 0.29 (0.03, 2.83) | 0.29 |
| NPM1 | 7 (3) | 6 (86) | 7.15 (0.85, 60.39) | 0.071 | 8.66 (1.00, 75.17) | 0.050 |
| ETV6 | 7 (3) | 4 (57) | 1.53 (0.33, 6.99) | 0.59 | 1.48 (0.32, 6.91) | 0.62 |
| TLR6 | 6 (3) | 1 (17) | 0.22 (0.03, 1.90) | 0.17 | 0.24 (0.03, 2.11) | 0.20 |
| WT1 | 7 (3) | 6 (86) | 7.15 (0.85, 60.39) | 0.071 | 8.36 (0.96, 72.99) | 0.055 |
| U2AF2 | 5 (2) | 2 (40) | 0.75 (0.12, 4.57) | 0.75 | 0.89 (0.14, 5.60) | 0.90 |
| TLR2 | 4 (2) | 1 (25) | 0.37 (0.04, 3.62) | 0.39 | 0.36 (0.04, 3.60) | 0.39 |
| GATA2 | 6 (3) | 4 (67) | 2.31 (0.41, 12.90) | 0.34 | 2.21 (0.39, 12.58) | 0.37 |
| TLR4 | 5 (2) | 2 (40) | 0.75 (0.12, 4.57) | 0.75 | 0.71 (0.11, 4.49) | 0.71 |
| MYBL2 | 5 (2) | 3 (60) | 1.72 (0.28, 10.49) | 0.56 | 1.85 (0.29, 11.65) | 0.51 |
| SF3B3 | 3 (1) | 2 (67) | 2.29 (0.20, 25.59) | 0.50 | 1.84 (0.16, 21.27) | 0.63 |
| SUZ12 | 5 (2) | 2 (40) | 0.75 (0.12, 4.57) | 0.75 | 0.72 (0.12, 4.55) | 0.73 |
| CDK6 | 3 (1) | 2 (67) | | | | |
| SF3B2 | 4 (2) | 4 (100) | | | | |
| CEBPA | 2 (1) | 0 (0) | | | | |
| DDX42 | 3 (1) | 1 (33) | | | | |
| TERT | 3 (1) | 1 (33) | | | | |
| EED | 3 (1) | 0 (0) | | | | |
| HNRNPA2B1 | 3 (1) | 1 (33) | | | | |
| PRPF40B | 2 (1) | 1 (50) | | | | |
| LUC7L2 | 2 (1) | 2 (100) | | | | |
| SF3B14 | 1 (1) | 0 (0) | | | | |
| NCSTN | 1 (1) | 0 (0) | | | | |
| APH1A | 1 (1) | 0 (0) | | | | |
| SF3A1 | 2 (1) | 2 (100) | | | | |
| SF3B4 | 2 (1) | 2 (100) | | | | |
| SFRS5 | 1 (1) | 1 (100) | | | | |
| MPL | 0 (0) | 0 (0) | | | | |
| CBLB | 1 (1) | 1 (100) | | | | |
| SF1 | 0 (0) | 0 (0) | | | | |
| MYD88 | 1 (1) | 1 (100) | | | | |
| RBBP4 | 0 (0) | 0 (0) | | | | |
| SF3A2 | 1 (1) | 1 (100) | | | | |
| TERC | 1 (1) | 1 (100) | | | | |
| BRAF | 0 (0) | 0 (0) | | | | |
| SFRS1 | 0 (0) | 0 (0) | | | | |
| GNAS | 1 (1) | 0 (0) | | | | |
| KIT | 1 (1) | 1 (100) | | | | |
| SPOP | 1 (1) | 1 (100) | | | | |
| DKC1 | 0 (0) | 0 (0) | | | | |

†Adjusted for age, sex, IPSS

TABLE 16

Final Logistic Regression Model from Stepwise Procedure.
Candidate variables included age (<70 vs. >=70
yrs), sex, IPSS (low/int1 vs. int-2/high), and all mutations.

| Gene | Unadjusted OR (95% CI) | p-value | Final Model Adjusted OR† (95% CI) | p-value |
|---|---|---|---|---|
| TET2 vs. WT | 1.99 (1.05, 3.80) | 0.036 | 1.99 (1.05, 3.80) | 0.036 |

TABLE 17

Response Rate versus Mutational Status Logistic Regression (modeling the
probability of response) adjusted models include age (>=70 yrs.
vs. <70), sex, IPSS (low/int-1 vs. int-2/high) and treatment
Note: Higher OR indicates a higher probability of response (OR > 1)
whereas lower OR indicates response less likely with the mutation.
Note: For the following comparisons the reference group is ANY of the other groups.

| Gene | N Mutations (%) | N (%) Response | Unadjusted OR (95% CI) | p-value | Adjusted OR† (95% CI) | p-value |
|---|---|---|---|---|---|---|
| ASXL1 (vs. WT for OR) | 91 (43) | 38 (42) | 0.69 (0.40, 1.20) | 0.19 | 0.68 (0.38, 1.19) | 0.17 |
| TET2 vs. (vs. WT for OR) | 50 (23) | 30 (60) | 1.99 (1.05, 3.80) | 0.036 | 1.98 (1.02, 3.85) | 0.044 |
| ASXL1wt + TET2 (vs. Other for OR) | 23 (11) | 17 (74) | 3.65 (1.38, 9.67) | 0.009 | 3.64 (1.35, 9.79) | 0.011 |
| ASXL1 + TET2wt (vs. Other for OR) | 64 (30) | 25 (39) | 0.63 (0.35, 1.15) | 0.13 | 0.63 (0.34, 1.16) | 0.14 |
| ASXL1 + TET2 (vs. Other for OR) | 27 (13) | 13 (48) | 1.06 (0.47, 2.37) | 0.89 | 1.03 (0.44, 2.38) | 0.95 |
| No ASXL1 or TET2 (vs. Other for OR) | 99 (46) | 45 (45) | 0.89 (0.52, 1.53) | 0.68 | 0.91 (0.52, 1.59) | 0.73 |

TABLE 17

146 Patients with Outcome Data (non-Daco trial pts) (≥3%; 5 or more muts)

| Gene with Mutation | N Pts w/a Mutation (%) | Univariate† HR (95% CI) | p-value† | IPSS and Trt Adjusted† HR (95% CI) | p-value† |
|---|---|---|---|---|---|
| N pts | 146 | | | | |
| ASXL1 | 67 (46) | 1.33 (0.91-1.93) | 0.14 | 1.41 (0.96-2.07) | 0.079 |
| TET2 | 35 (24) | 0.83 (0.54-1.27) | 0.39 | 0.87 (0.57-1.33) | 0.52 |
| RUNX1 | 26 (18) | 1.04 (0.65-1.67) | 0.86 | 0.96 (0.60-1.54) | 0.86 |
| TP53 | 29 (20) | 2.46 (1.55-3.92) | <0.001 | 2.45 (1.51-3.98) | <0.001 |
| SRSF2 | 25 (17) | 1.01 (0.63-1.60) | 0.98 | 1.05 (0.65-1.68) | 0.85 |
| DNMT3A | 24 (16) | 0.96 (0.60-1.54) | 0.85 | 0.75 (0.45-1.24) | 0.25 |
| SF3B1 | 17 (12) | 1.02 (0.57-1.83) | 0.94 | 0.96 (0.53-1.73) | 0.89 |
| U2AF1 | 21 (14) | 1.04 (0.61-1.76) | 0.90 | 1.10 (0.64-1.88) | 0.73 |
| NOTCH2 | 18 (12) | 0.67 (0.38-1.21) | 0.18 | 0.65 (0.36-1.16) | 0.14 |
| NRAS | 10 (7) | 0.68 (0.32-1.47) | 0.33 | 0.65 (0.30-1.41) | 0.27 |
| BCOR | 12 (8) | 1.08 (0.56-2.07) | 0.82 | 0.98 (0.51-1.90) | 0.96 |
| NF1 | 12 (8) | 0.86 (0.42-1.79) | 0.69 | 0.92 (0.42-2.04) | 0.84 |
| EZH2 | 12 (8) | 1.24 (0.64-2.37) | 0.52 | 1.57 (0.79-3.09) | 0.20 |
| MAML1 | 10 (7) | 1.37 (0.72-2.63) | 0.34 | 1.31 (0.68-2.54) | 0.43 |
| NOTCH1 | 12 (8) | 0.64 (0.31-1.34) | 0.24 | 0.70 (0.33-1.48) | 0.34 |
| IDH2 | 5 (3) | 0.87 (0.32-2.38) | 0.79 | 0.93 (0.34-2.54) | 0.88 |
| SCAF11 | 11 (8) | 1.04 (0.52-2.05) | 0.92 | 0.92 (0.46-1.85) | 0.81 |
| KDM6B | 9 (6) | 0.75 (0.31-1.84) | 0.53 | 0.60 (0.24-1.51) | 0.28 |
| CBL | 7 (5) | 1.29 (0.57-2.94) | 0.54 | 1.29 (0.55-3.01) | 0.56 |
| TLR1 | 10 (7) | 1.08 (0.52-2.21) | 0.84 | 1.04 (0.51-2.14) | 0.92 |
| ATRX | 4 (3) | 1.40 (0.44-4.42) | 0.57 | 1.82 (0.55-5.99) | 0.32 |
| KDM3A | 5 (3) | 1.70 (0.69-4.20) | 0.25 | 1.52 (0.61-3.79) | 0.37 |
| PHF6 | 4 (3) | 0.72 (0.23-2.28) | 0.57 | 0.70 (0.22-2.26) | 0.55 |

TABLE 17-continued

146 Patients with Outcome Data (non-Daco trial pts) (≥3%; 5 or more muts)

| Gene with Mutation | N Pts w/a Mutation (%) | Univariate† HR (95% CI) | p-value† | IPSS and Trt Adjusted† HR (95% CI) | p-value† |
|---|---|---|---|---|---|
| PRPF8 | 4 (3) | 1.33 (0.49-3.63) | 0.58 | 1.56 (0.56-4.37) | 0.39 |
| PTPN11 | 2 (1) | 2.68 (0.65-11.01) | 0.17 | 1.99 (0.47-8.35) | 0.35 |
| IDH1 | 6 (4) | 0.94 (0.38-2.31) | 0.89 | 0.98 (0.40-2.44) | 0.98 |
| JAK2 | 7 (5) | 0.63 (0.25-1.57) | 0.32 | 0.59 (0.24-1.48) | 0.26 |
| KRAS | 4 (3) | 1.09 (0.27-4.44) | 0.90 | 2.33 (0.56-9.71) | 0.25 |
| NPM1 | 5 (3) | 0.66 (0.21-2.10) | 0.49 | 0.67 (0.21-2.13) | 0.50 |
| TLR6 | 6 (4) | 0.97 (0.36-2.62) | 0.94 | 0.92 (0.34-2.51) | 0.87 |
| MYBL2 | 5 (3) | 0.87 (0.32-2.37) | 0.79 | 0.97 (0.35-2.68) | 0.95 |

†Compared to group without that mutation
††Adjusted for IPSS and Treatment 2 pts. with unknown IPSS are excluded.

TABLE 18

Final Cox Regression Model from Stepwise Procedure. Candidate variables included age (<70 vs. >=70 yrs), sex, IPSS (low/int1 vs. int-2/high), and all mutations (≥3%; 5 or more muts) (note with survival definition changed, ASXL1 was not in final model)

| Gene | Adjusted HR† (95% CI) | p-value |
|---|---|---|
| TP53 vs. WT | 2.46 (1.55, 3.92) | <0.001 |

TABLE 19

Number of Mutations for Combinations of ASXL1 vs. TET2 for those with Survival Data

| Gene | N Mutations (%) |
|---|---|
| N pts | 146 |
| ASXL1 | 67 (46) |
| TET2 | 35 (24) |
| ASXL1 wt + TET2 | 15 (10) |
| ASXL1 + TET2 wt | 47 (32) |
| ASXL1 + TET2 | 20 (14) |
| No ASXL1 or TET2 | 64 (44) |

TABLE 20

Univariate Cox Regression Models for OS for 146 Patients (non-Daco trial pts) Comparing Combinations of ASXL1 and TET2

| Gene | Univariate† HR (95% CI) | p-value |
|---|---|---|
| N pts | 146 | |
| ASXL1 vs. WT | 1.33 (0.91-1.93) | 0.14 |
| TET2 vs. WT | 0.83 (0.54-1.27) | 0.39 |

TABLE 20-continued

Univariate Cox Regression Models for OS for 146 Patients (non-Daco trial pts) Comparing Combinations of ASXL1 and TET2

| Gene | Univariate† HR (95% CI) | p-value |
|---|---|---|
| ASXL1 wt+ TET2 vs. Other | 0.59 (0.32-1.11) | 0.10 |
| ASXL1 + TET2 wt vs. Other | 1.26 (0.85-1.86) | 0.25 |
| ASXL1 + TET2 vs. Other | 1.20 (0.70-1.97) | 0.54 |
| No ASXL1 or TET2 vs. Other | 0.95 (0.66-1.38) | 0.80 |

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of this disclosure and these claims.

We claim:

1. A method for treating subjects with myelodysplastic syndrome with hypomethylating agents, comprising:
   determining whether a subject with a myelodysplastic syndrome has a somatic mutation in TET2 having a variant allele fraction (VAF) greater than 10% and does not have a somatic mutation in ASXL1, wherein the somatic mutations are determined or have been determined by sequencing a nucleic acid sample obtained from the subject; and
   administering an effective amount of a hypomethylating agent to the subject when both a somatic mutation in TET2 having a VAF greater than 10% is detected and a somatic mutation in ASXL1 is not detected.

2. The method of claim 1, wherein the VAF is measured by a method selected from the group consisting of Next-Generation sequencing, Mass spectrometry genotyping, real time polymerase chain reaction, Sanger sequencing, single nucleotide polymorphism (SNP) arrays, and interphase fluorescent in situ hybridization (FISH) analysis.

3. The method of claim 1, wherein the nucleic acid sample is isolated from blood, bone marrow or a blood fraction obtained from the subject.

4. The method of claim 1, further comprising obtaining the sample from the subject.

5. The method of claim 1, wherein determining somatic mutations is performed by Next-Generation genomic sequencing and/or Mass spectrometry genotyping.

6. The method of claim 1, wherein the hypomethylating agent comprises azacytidine and/or decitabine.

7. The method of claim 1, wherein the somatic mutations are determined or have been determined by sequencing a nucleic acid sample obtained from the subject and enriched for nucleic acids encoding for ASXL1 and TET2; aligning the sequences to the human genome; and discarding synonymous variants, non-coding variants more than 6 bases from splice junctions, or variants present in databases selected from dbSNP 132 and NHLBI Exome Sequencing Project at a population frequency of 1% or more.

* * * * *

UNITED STATES PATENT AND TRADEMARK OFFICE
CERTIFICATE OF CORRECTION

| | | |
|---|---|---|
| PATENT NO. | : 11,015,223 B2 | |
| APPLICATION NO. | : 14/888389 | |
| DATED | : May 25, 2021 | |
| INVENTOR(S) | : Rafael Bejar et al. | |

It is certified that error appears in the above-identified patent and that said Letters Patent is hereby corrected as shown below:

On the Title Page

Column 1, item [73] Line 6, "HOSPITAT. INC.," should be -- HOSPITAL, INC., --
Column 2, item [56] Line 4, "11,," should be -- 11, --
Column 2, item [56] Line 20, "Haematologica" should be -- Haematologica, --

In the Specification

Column 1, Line 7, After "application" insert -- is the U.S. National Stage of International Application No. PCT/US2014/037717, filed May 12, 2014, published in English under PCT Article 21(2), which --
Column 1, Lines 14-21 (approx.), "This application is the U.S. National Stage of International Application No. PCT/US2014/037717, filed May 12, 2014, published in English under PCT Article 21(2), which claims the priority benefit of the earlier filing date of U.S. Provisional Application No. 61/822,159, filed May 10, 2013, which is hereby incorporated herein by reference in its entirety." should be -- This invention was made with government support under grant numbers 5K08DK091360-03 and R01HL082945 both awarded by the National Institutes of Health. The government has certain rights in the invention. --
Column 4, Line 2, "6,033,881" should be -- 6,033,881), --
Column 6, Lines 49-50, "subject's response to the a" should be -- subjects response to a --
Column 6, Line 51, "synactic" should be -- syntactic --
Column 9, Line 11, "5-(carboxyhydroxylmethyl)" should be -- 5-(carboxyhydroxymethyl) --
Column 9, Lines 13-14, "beta-D-galactosylqueosine," should be -- beta-D-galactosylqueuosine, --
Column 9, Line 14, "N~6-sopentenyladenine," should be -- N~6-isopentenyladenine, --
Column 9, Line 18, "methoxyarninomethyl-2-thiouracil," should be -- methoxyaminomethyl-2-thiouracil, --
Column 9, Line 19, "beta-D-mannosylqueosine," should be -- beta-D-mannosylqueuosine, --
Column 9, Line 21, "queosine," should be -- queuosine, --
Column 9, Line 33, "phosphordiamidate," should be -- phosphorodiamidate, --
Column 11, Line 2, "urine," should be -- urine. --

Signed and Sealed this
Ninth Day of August, 2022

*Katherine Kelly Vidal*

Katherine Kelly Vidal
*Director of the United States Patent and Trademark Office*

CERTIFICATE OF CORRECTION (continued)
U.S. Pat. No. 11,015,223 B2

Column 11, Line 60, "2d" should be -- 2nd --
Column 11, Line 62, "3d" should be -- 3rd --
Column 12, Line 6, "limiting" should be -- limiting. --
Column 18, Line 23, "96/17958." should be -- 96/17958). --
Column 19, Line 17, "(NASBAO," should be -- (NASBA, --
Column 23, Line 47, "47%)." should be -- 47%), --
Column 24, Line 49, "Hi Seq" should be -- HiSeq --
Column 26, Line 40, "Including," should be -- Including --
Column 27, Line 32, "al" should be -- al. --
Column 33, Line 2 (Table 9), "al" should be -- all --
Column 33, Line 5 (Table 10), "w/a" should be -- w/ a --
Column 34, Line 5 (Table 10-Continued), "w/a" should be -- w/ a --
Column 39, Line 44, "w/a" should be -- w/ a --
Column 40, Line 44, "w/a" should be -- w/ a --